US 7,623,913 B2

(12) United States Patent
Phillips

(10) Patent No.: US 7,623,913 B2
(45) Date of Patent: Nov. 24, 2009

(54) IMPLANTABLE MEDICAL DEVICES USING HEURISTIC FILTERING IN CARDIAC EVENT DETECTION

(75) Inventor: James William Phillips, Fountain Valley, CA (US)

(73) Assignee: Cameron Health, Inc., San Clemente, CA (US)

( * ) Notice: Subject to any disclaimer, the term of this patent is extended or adjusted under 35 U.S.C. 154(b) by 501 days.

(21) Appl. No.: 11/497,204

(22) Filed: Aug. 1, 2006

(65) Prior Publication Data

US 2008/0045850 A1    Feb. 21, 2008

(51) Int. Cl.
*A61B 5/0402*    (2006.01)
*A61N 1/362*    (2006.01)

(52) U.S. Cl. .......................... 600/517; 600/509; 607/9; 341/61

(58) Field of Classification Search ................ 367/45; 708/322–323; 375/130, 145, 149, 232, 295, 375/376; 600/508–528; 607/9; 128/901, 128/902; 70/260; 341/61
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |

(Continued)

FOREIGN PATENT DOCUMENTS

DE    298 01 807 U1    7/1998

(Continued)

OTHER PUBLICATIONS

Haykin, Simon. Adaptive Filter Theory, Fourth Edition. Prentice Hall 2002.*

(Continued)

*Primary Examiner*—Carl H Layno
*Assistant Examiner*—Luther G Behringer
(74) *Attorney, Agent, or Firm*—Pramudji Wendt & Tran, LLP; Ari Pramudji; Mark Schroeder

(57) ABSTRACT

Methods for performing cardiac signal analysis in an implanted medical device, and devices configured to perform illustrative methods of cardiac signal analysis. A cardiac signal is captured by an implanted device using implanted electrodes and, during at least certain conditions, the cardiac signal undergoes heuristic filtering. In some embodiments, heuristic filtering is achieved by modifying a signal or value that is used as an indicator of received signal amplitude. In an illustrative example, the heuristic filtering includes periodically incrementing or decrementing the signal or value toward a desired quiescent point, where the heuristic filter period is significantly longer than the sampling period for the signal itself. In another illustrative example, the heuristic filter frequency can be adjusted dynamically to keep the signal average near the desired quiescent point.

12 Claims, 25 Drawing Sheets

U.S. PATENT DOCUMENTS

| | | | |
|---|---|---|---|
| 4,254,775 A | 3/1981 | Langer | |
| 4,291,707 A | 9/1981 | Heilman et al. | |
| 4,300,567 A | 11/1981 | Kolenik et al. | |
| 4,314,095 A | 2/1982 | Moore et al. | |
| 4,375,817 A | 3/1983 | Engle et al. | |
| 4,387,465 A * | 6/1983 | Becker | 375/130 |
| 4,402,322 A | 9/1983 | Duggan | |
| 4,407,288 A | 10/1983 | Langer et al. | |
| 4,424,818 A | 1/1984 | Doring et al. | |
| 4,450,527 A | 5/1984 | Sramek | |
| 4,509,529 A | 4/1985 | Money et al. | |
| 4,527,133 A | 7/1985 | Money | |
| 4,548,209 A | 10/1985 | Wielders et al. | |
| 4,567,883 A | 2/1986 | Langer et al. | |
| 4,567,900 A | 2/1986 | Moore | |
| 4,595,009 A | 6/1986 | Leinders | |
| 4,602,637 A | 7/1986 | Elmqvist et al. | |
| 4,603,705 A | 8/1986 | Speicher et al. | |
| 4,692,719 A | 9/1987 | Whigham | |
| 4,693,253 A | 9/1987 | Adams | |
| 4,727,877 A | 3/1988 | Kallok | |
| 4,750,494 A | 6/1988 | King | |
| 4,765,341 A | 8/1988 | Mower et al. | |
| 4,768,512 A | 9/1988 | Imran | |
| 4,800,883 A | 1/1989 | Winstrom | |
| 4,819,252 A * | 4/1989 | Christopher | 375/240 |
| 4,830,005 A | 5/1989 | Woskow | |
| 4,944,300 A | 7/1990 | Saksena | |
| 5,014,284 A | 5/1991 | Langer et al. | |
| 5,044,374 A | 9/1991 | Lindemans et al. | |
| 5,105,810 A | 4/1992 | Collins et al. | |
| 5,105,826 A | 4/1992 | Smits et al. | |
| 5,109,842 A | 5/1992 | Adinolfi | |
| 5,129,392 A | 7/1992 | Bardy et al. | |
| 5,133,353 A | 7/1992 | Hauser | |
| 5,144,946 A | 9/1992 | Weinberg et al. | |
| 5,184,616 A | 2/1993 | Weiss | |
| 5,191,901 A | 3/1993 | Dahl et al. | |
| 5,203,348 A | 4/1993 | Dahl et al. | |
| 5,215,081 A | 6/1993 | Ostroff | |
| 5,230,337 A | 7/1993 | Dahl et al. | |
| 5,255,692 A | 10/1993 | Neubauer et al. | |
| 5,261,400 A | 11/1993 | Bardy | |
| 5,300,106 A | 4/1994 | Dahl et al. | |
| 5,301,677 A | 4/1994 | Hsung | |
| 5,313,953 A | 5/1994 | Yomtov et al. | |
| 5,331,966 A | 7/1994 | Bennett et al. | |
| 5,342,407 A | 8/1994 | Dahl et al. | |
| 5,366,496 A | 11/1994 | Dahl et al. | |
| 5,376,103 A | 12/1994 | Anderson et al. | |
| 5,376,104 A | 12/1994 | Sakai et al. | |
| 5,385,574 A | 1/1995 | Hauser et al. | |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,439,485 A | 8/1995 | Mar et al. | |
| 5,447,521 A | 9/1995 | Anderson et al. | |
| 5,476,503 A | 12/1995 | Yang | |
| 5,509,923 A | 4/1996 | Middleman et al. | |
| 5,509,928 A | 4/1996 | Acken | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,573,003 A | 11/1996 | Mann et al. | |
| 5,597,956 A | 1/1997 | Ito et al. | |
| 5,601,607 A | 2/1997 | Adams | |
| 5,603,732 A | 2/1997 | Dahl et al. | |
| 5,607,455 A | 3/1997 | Armstrong | |
| 5,618,287 A | 4/1997 | Fogarty et al. | |
| 5,620,477 A | 4/1997 | Pless et al. | |
| 5,642,377 A * | 6/1997 | Chung et al. | 375/145 |
| 5,643,328 A | 7/1997 | Cooke et al. | |
| 5,645,586 A | 7/1997 | Meltzer | |
| 5,658,317 A * | 8/1997 | Haefner et al. | 607/5 |
| 5,658,319 A | 8/1997 | Kroll | |
| 5,658,321 A | 8/1997 | Fayram et al. | |
| 5,674,260 A | 10/1997 | Weinberg | |
| 5,690,648 A | 11/1997 | Fogarty et al. | |
| 5,690,683 A | 11/1997 | Haefner et al. | |
| 5,697,953 A | 12/1997 | Kroll et al. | |
| 5,713,926 A | 2/1998 | Hauser et al. | |
| 5,748,120 A * | 5/1998 | Yasuda | 341/61 |
| 5,766,226 A | 6/1998 | Pedersen | |
| 5,776,169 A | 7/1998 | Schroeppel | |
| 5,814,090 A | 9/1998 | Latterell et al. | |
| 5,827,326 A | 10/1998 | Kroll et al. | |
| 5,836,976 A | 11/1998 | Min et al. | |
| 5,843,132 A | 12/1998 | Ilvento | |
| 5,895,414 A | 4/1999 | Sanchez-Zambrano | |
| 5,904,705 A | 5/1999 | Kroll et al. | |
| 5,919,211 A | 7/1999 | Adams | |
| 5,919,222 A | 7/1999 | Hjelle et al. | |
| 5,924,980 A * | 7/1999 | Coetzee | 600/300 |
| 5,925,069 A | 7/1999 | Graves et al. | |
| 5,935,154 A | 8/1999 | Westlund | |
| 5,941,904 A | 8/1999 | Johnston et al. | |
| 5,953,018 A * | 9/1999 | Lam | 345/440 |
| 5,957,956 A | 9/1999 | Kroll et al. | |
| 6,014,586 A | 1/2000 | Weinberg et al. | |
| 6,026,325 A | 2/2000 | Weinberg et al. | |
| 6,058,328 A | 5/2000 | Levine et al. | |
| 6,093,173 A | 7/2000 | Balceta et al. | |
| 6,095,987 A | 8/2000 | Shmulewitz et al. | |
| H1905 H | 10/2000 | Hill | |
| 6,128,531 A | 10/2000 | Campbell-Smith | |
| 6,144,866 A | 11/2000 | Miesel et al. | |
| 6,144,879 A | 11/2000 | Gray | |
| 6,148,230 A | 11/2000 | KenKnight | |
| 6,185,450 B1 | 2/2001 | Seguine et al. | |
| 6,216,031 B1 * | 4/2001 | Findeis et al. | 600/509 |
| 6,266,567 B1 | 7/2001 | Ishikawa et al. | |
| 6,278,894 B1 | 8/2001 | Salo et al. | |
| 6,280,462 B1 | 8/2001 | Hauser et al. | |
| 6,286,346 B1 * | 9/2001 | Hocken et al. | 70/260 |
| 6,334,071 B1 | 12/2001 | Lu | |
| 6,345,198 B1 | 2/2002 | Mouchawar et al. | |
| 6,370,430 B1 * | 4/2002 | Mika et al. | 607/9 |
| 6,411,844 B1 | 6/2002 | Kroll et al. | |
| 6,647,292 B1 | 11/2003 | Bardy et al. | |
| 6,708,059 B1 * | 3/2004 | Radeztsky | 600/523 |
| 6,721,597 B1 | 4/2004 | Bardy et al. | |
| 6,747,581 B2 * | 6/2004 | Hodges | 341/61 |
| 6,754,528 B2 | 6/2004 | Bardy et al. | |
| 6,778,860 B2 | 8/2004 | Ostroff et al. | |
| 6,788,974 B2 | 9/2004 | Bardy et al. | |
| 6,834,204 B2 | 12/2004 | Ostroff et al. | |
| 6,856,835 B2 | 2/2005 | Bardy et al. | |
| 6,865,417 B2 | 3/2005 | Rissmann et al. | |
| 6,866,044 B2 | 3/2005 | Bardy et al. | |
| 6,927,721 B2 | 8/2005 | Ostroff et al. | |
| 6,937,907 B2 | 8/2005 | Bardy et al. | |
| 6,950,705 B2 | 9/2005 | Bardy et al. | |
| 6,952,608 B2 | 10/2005 | Ostroff | |
| 6,952,610 B2 | 10/2005 | Ostroff et al. | |
| 6,954,670 B2 | 10/2005 | Ostroff | |
| 6,988,003 B2 | 1/2006 | Bardy et al. | |
| 7,020,523 B1 | 3/2006 | Lu et al. | |
| 7,027,858 B2 | 4/2006 | Cao et al. | |
| 7,039,459 B2 | 5/2006 | Bardy et al. | |
| 7,039,463 B2 | 5/2006 | Marcovecchio | |

| | | | |
|---|---|---|---|
| 7,043,299 | B2 | 5/2006 | Erlinger et al. |
| 7,062,329 | B2 | 6/2006 | Ostroff et al. |
| 7,065,407 | B2 | 6/2006 | Bardy et al. |
| 7,065,410 | B2 | 6/2006 | Bardy et al. |
| 7,069,080 | B2 | 6/2006 | Bardy et al. |
| 7,076,294 | B2 | 7/2006 | Bardy et al. |
| 7,076,296 | B2 | 7/2006 | Rissmann et al. |
| 7,090,682 | B2 | 8/2006 | Sanders et al. |
| 7,092,754 | B2 | 8/2006 | Bardy et al. |
| 7,345,607 | B1 | 3/2008 | Frigaard et al. |
| 2001/0027330 | A1 | 10/2001 | Sullivan et al. |
| 2003/0135125 | A1* | 7/2003 | Lu et al. ............ 600/510 |
| 2004/0254611 | A1 | 12/2004 | Palreddy et al. |
| 2004/0254613 | A1 | 12/2004 | Ostroff et al. |
| 2005/0049644 | A1 | 3/2005 | Warren et al. |
| 2006/0079796 | A1 | 4/2006 | Marcovecchio et al. |
| 2006/0085038 | A1 | 4/2006 | Linder et al. |

FOREIGN PATENT DOCUMENTS

| | | |
|---|---|---|
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | 2002 024275 A3 | 5/2002 |
| WO | WO 02/068046 A1 | 9/2002 |
| WO | WO 03/018121 A2 | 3/2003 |

OTHER PUBLICATIONS

Information Disclosure statement (postcard, transmittal, and PTO-1449), originally submitted Nov. 2006 (postcard shows receipt by USPTO on Nov. 17, 2006)—foreign and NPL references not accounted for in USPTO records are included herewith (2 each).

Schuder et al.; "Standby Implanted Defibrillators"; Arch Intern. Med; vol. 127, p. 317; Feb. 1971.

Schuder; "Completely Implanted Defibrillator"; JAMA; vol. 214, No. 6, p. 1123; Nov. 9, 1970.

Bardy, Gust H. et al., "Multicenter Experience with a Pectoral Unipolar Implantable Cardioverter-Defibrillator," *JACC*, Aug. 1996, vol. 28, No. 2, pp. 400-410.

Friedman, Richard A. et al., "Implantable Defibrillators In Children: From Whence to Shock," *Journal of Cardiovascular Electrophysiology*, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Higgins, Steven L. et al., "The First Year Experience with the Dual Chamber ICD," *Pace*, Jan. 2000, vol. 23, pp. 18-25.

Mirowski, M. et al., "Automatic Detection and Defibrillation of Lethal Arrhythmias-A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970. p. 1123 (single sheet).

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Schwacke, H. et al., "Komplikationen mit Sonden bei 340 Patienten mit einem Implantierbaren Kardioverter/Defibrillator," *Z Kardiol* (1999)vol. 88, No. 8, pp. 559-565.

Throne, Robert D. et al., "A Comparison of Four New Time-Domain Techniques for Discriminating Monomorphic Ventricular Tachycardia from Sinus Rhythm Using Ventricular Waveform Morphology," *IEEE Transactions on Biomedical Engineering*, vol. 38, No. 6, Jun. 1991, pp. 561-570.

Tietze U. et al., "Halbleiter-Schaltungstechnik," © Springer-Verlag (Berlin, Germany), (1991), pp. 784-786.

Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.

Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.

* cited by examiner

IMPLANTABLE MEDICAL DEVICES USING HEURISTIC FILTERING IN CARDIAC EVENT DETECTION

FIELD

The present invention relates to the field of medical devices. More particularly, the present invention relates to the field of implantable medical devices including circuitry for capturing, detecting, and analyzing cardiac events using electrical signals.

BACKGROUND

Implantable medical devices that electronically monitor cardiac activity are desirable for a variety of purposes. Some such devices undergo, for various reasons, monitoring operations in which sensing and detection of cardiac events may be temporarily suspended or in which a sensing vector comes into use after a period of disuse. For example, an implantable cardioverter-defibrillator (ICD) may use a blanking period following delivery of an electrical stimulus. On return from the blanking period, reestablishment of a baseline for small-signal sensing of cardiac activity in a predictable and quick manner is desired.

SUMMARY

The present invention, in illustrative embodiments, includes methods for performing cardiac signal analysis in an implanted medical device, and devices configured to perform illustrative methods of cardiac signal analysis. A cardiac signal is captured by an implanted device using implanted electrodes and, during at least certain conditions, the cardiac signal undergoes heuristic filtering. In some embodiments, heuristic filtering is achieved by modifying a signal or value that is used as an indicator of received signal amplitude. In an illustrative example, the heuristic filtering includes periodically incrementing or decrementing the signal or value toward a desired quiescent point, where the heuristic filter period is significantly longer than the sampling period for the signal itself. In another illustrative example, the heuristic filter frequency can be adjusted dynamically to keep the signal average near the desired quiescent point.

DETAILED DESCRIPTION

The following detailed description should be read with reference to the drawings. The drawings, which are not necessarily to scale, depict illustrative embodiments and are not intended to limit the scope of the invention.

As used herein, the term "heuristic" refers to a rule. A "heuristic filter" operates on the basis of a rule to adjust a value. This is in contrast to frequency selective filters that may be manifested in a number of ways in circuitry. For several of the examples given below, the heuristic of the heuristic filter is that a variable observed by the heuristic filter should be near a desired value. The meaning and application of this heuristic will become more apparent as the following description is read.

Figure 1A:
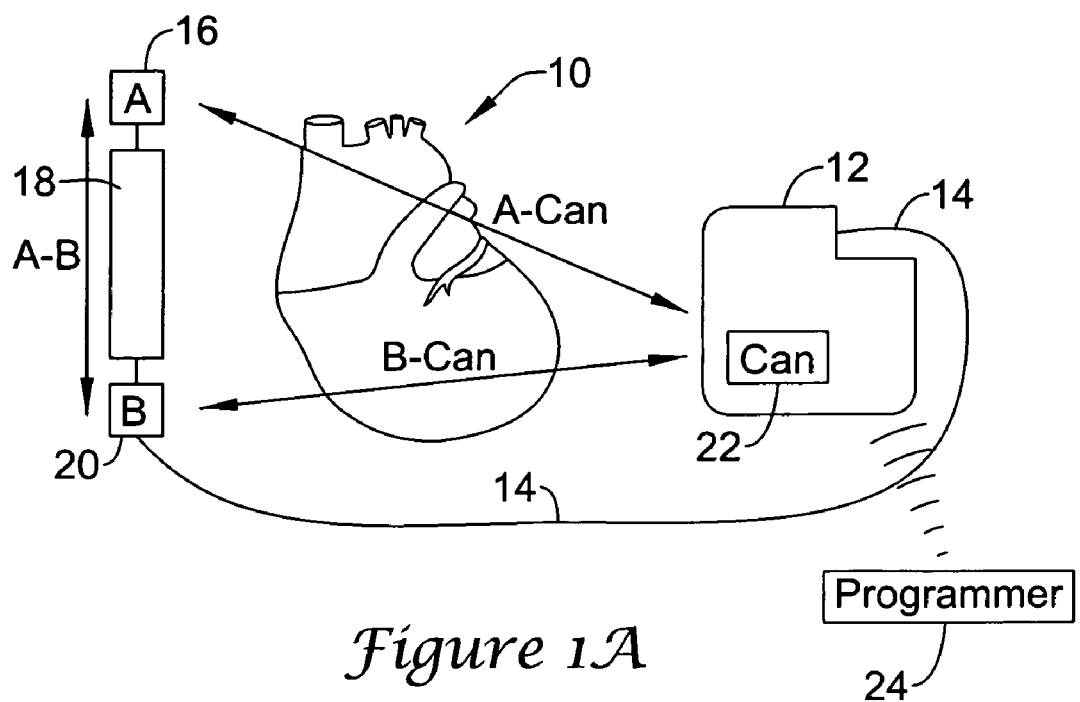
FIGS. 1A-1B illustrate, respectively, representative subcutaneous and intravenous ICD systems.
Figure 1B:
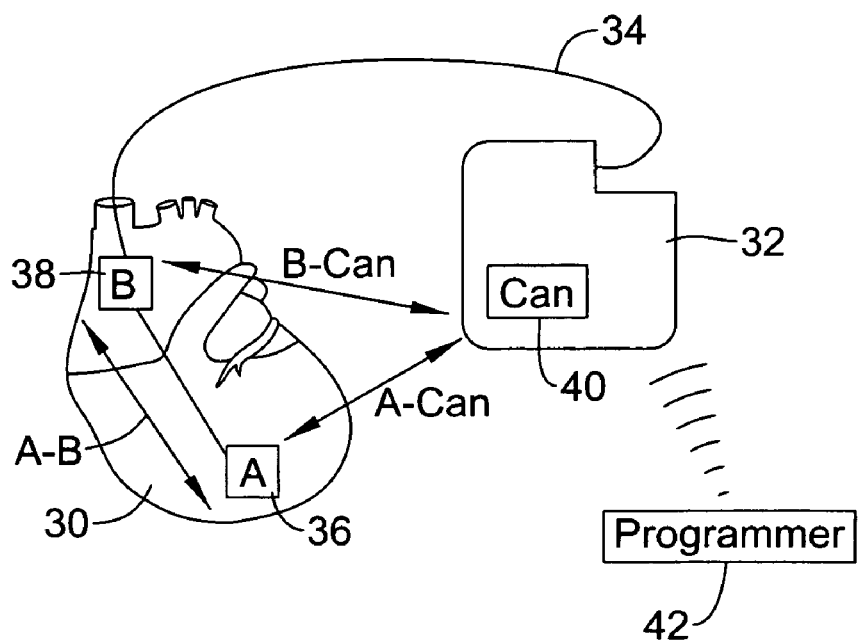

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister and includes sensing electrode A 16, coil electrode 18, and sensing electrode B 20. A can electrode 22 is shown on the canister 12.

Several vectors for sensing are therefore available including at least A-can, B-can, and A-B. It should be noted that the use of the coil electrode 18 as a sensing electrode is also possible. Illustrative subcutaneous systems are shown in U.S. Pat. Nos. 6,647,292 and 6,721,597, and the disclosures of these patents are incorporated herein by reference. Some embodiments include a unitary system having two or more electrodes on a housing as set forth in the '292 patent, rather than that which is shown. A unitary system including an additional lead may also be used.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. Additional electrodes for sensing or stimulus delivery may also be included in some embodiments of the present invention. In the illustrative example, electrode A 36 is located generally in the patient's ventricle, and electrode B 38 is located generally in the patient's atrium. The lead 34 may be anchored into the patient's myocardium. Again, a can electrode 40 is shown on the canister 32. With the transvenous system, plural sensing vectors may be defined as well.

For either subcutaneous or transvenous systems, a suitable method of selecting a sensing vector may be used, for example, as set forth in U.S. patent application Ser. No. 10/901,258, filed Jul. 27, 2004 and now U.S. Pat. No. 7,392,085, which is incorporated herein by reference. In both FIGS. 1A and 1B, one or more sensing electrodes may also be used for stimulus delivery, and multiple possible stimulus delivery vectors may be defined.

The systems shown in FIGS. 1A-1B may include operational circuitry and a power source housed within the respective canisters. The power source may be, for example, a battery or bank of batteries. The operational circuitry may be configured to include such controllers, microcontrollers, logic devices, memory, and the like, as selected, needed, or desired for performing the illustrative methods set forth herein. The operational circuitry may (although not necessarily) further include a charging sub-circuit and a power storage sub-circuit (for example, a capacitor or a bank of capacitors) for building up a stored charge. The operational circuitry may also be adapted to provide a pacing output. Either or both cardioversion/defibrillation and pacing sub-circuitry and capacities may be incorporated into a single device. The methods discussed below may also be embodied in hardware within the operational circuitry and/or as instruction sets for operating the operational circuitry and/or in the form of machine-readable media (optical, electrical, magnetic, etc.) embodying such instructions and instruction sets.

Each of the devices 12, 32 may further include such components as would be appropriate for communication (typically via RF) with an external device such as a programmer. To this end, programmers 24 (FIG. 1A) and 42 (FIG. 1B) are also shown. For example, during an implantation procedure, once the implantable device 24, 42 and leads (if included) are placed, the programmer 24, 42 may be used to activate and/or direct and/or observe diagnostic or operational tests. After implantation, the programmer 24, 42 may be used to non-invasively determine the status and history of the implanted device 12, 32 and to upgrade programming of the implanted device 12, 32. The programmer 24, 42 and the implanted devices 12, 32 are adapted for wireless communication allowing interrogation of the implanted device(s). The programmers 24, 42 in combination with the implanted devices 12, 32 may also allow annunciation of statistics, errors, history and existing or potential problems to the user/physician.

Figure 2:
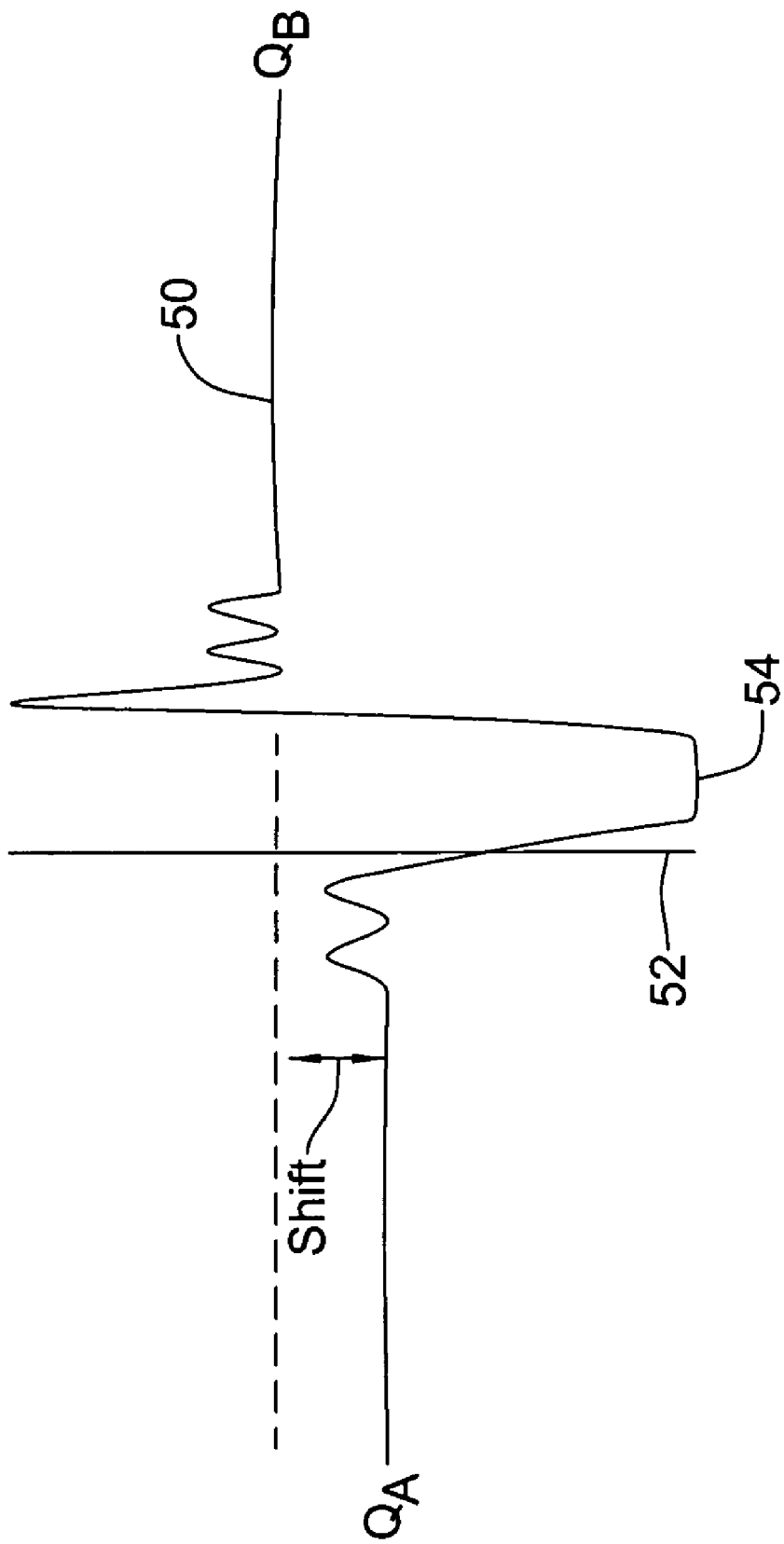
FIG. 2 illustrates the effect of post-shock afterpotential on cardiac monitoring in an implantable medical device system.

FIG. 2 illustrates the effect of post-shock afterpotential on cardiac monitoring in an implantable medical device system. A rough cardiac signal, which could be sensed by implanted electrodes, is shown generally at 50, with a shock being delivered at time 52, resulting in saturation 54. Prior to shock delivery, the signal 50 traverses a path, in accordance with the patient's cardiac functions, about a first quiescent point $Q_A$, while after the shock delivery, the signal 50 oscillates about a second quiescent point $Q_B$. The result is a shift in the baseline.

Figure 3:
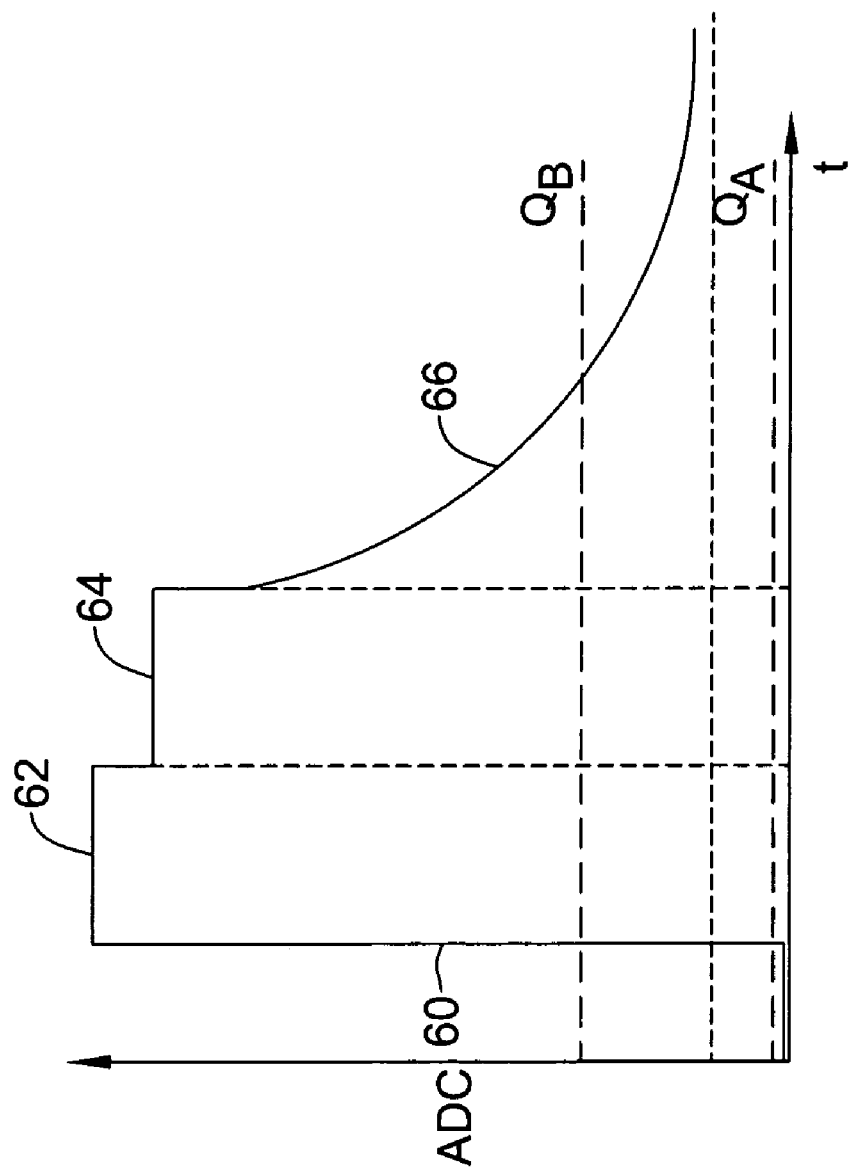
FIG. 3 is a graph of an illustrative detection profile.

The baseline shift may become relevant when cardiac event detection is occurring. Referring to FIG. 3, a detection profile is shown generally by line 60. The detection profile is used to determine whether and when the received cardiac signal likely indicates a cardiac event. When the detection profile 60 is crossed by the incoming signal, a detection occurs. The existence of a detection starts analysis of the signal near the detection. The detection profile 60 includes a refractory period 62 during which detections do not occur. The refractory period 62 follows a previous detection. The illustrative detection profile 60 includes a continuation period 64 that follows the refractory period 62, during which the detection threshold remains relatively high. The detection profile includes a decay period 66, during which the detection threshold follows an exponentially decaying profile toward a detection floor. The particulars of a detection profile 60 may be selected as desired.

As can be seen, the detection profile 60 is configured to work well when a first quiescent point $Q_A$ exists. However, the second quiescent point $Q_B$ can cause a detection profile 60 to be crossed even without a cardiac event occurring. It may be desirable for the system to operate with a consistent quiescent point that readily aligns with the detection profile 60.

Figure 4A:
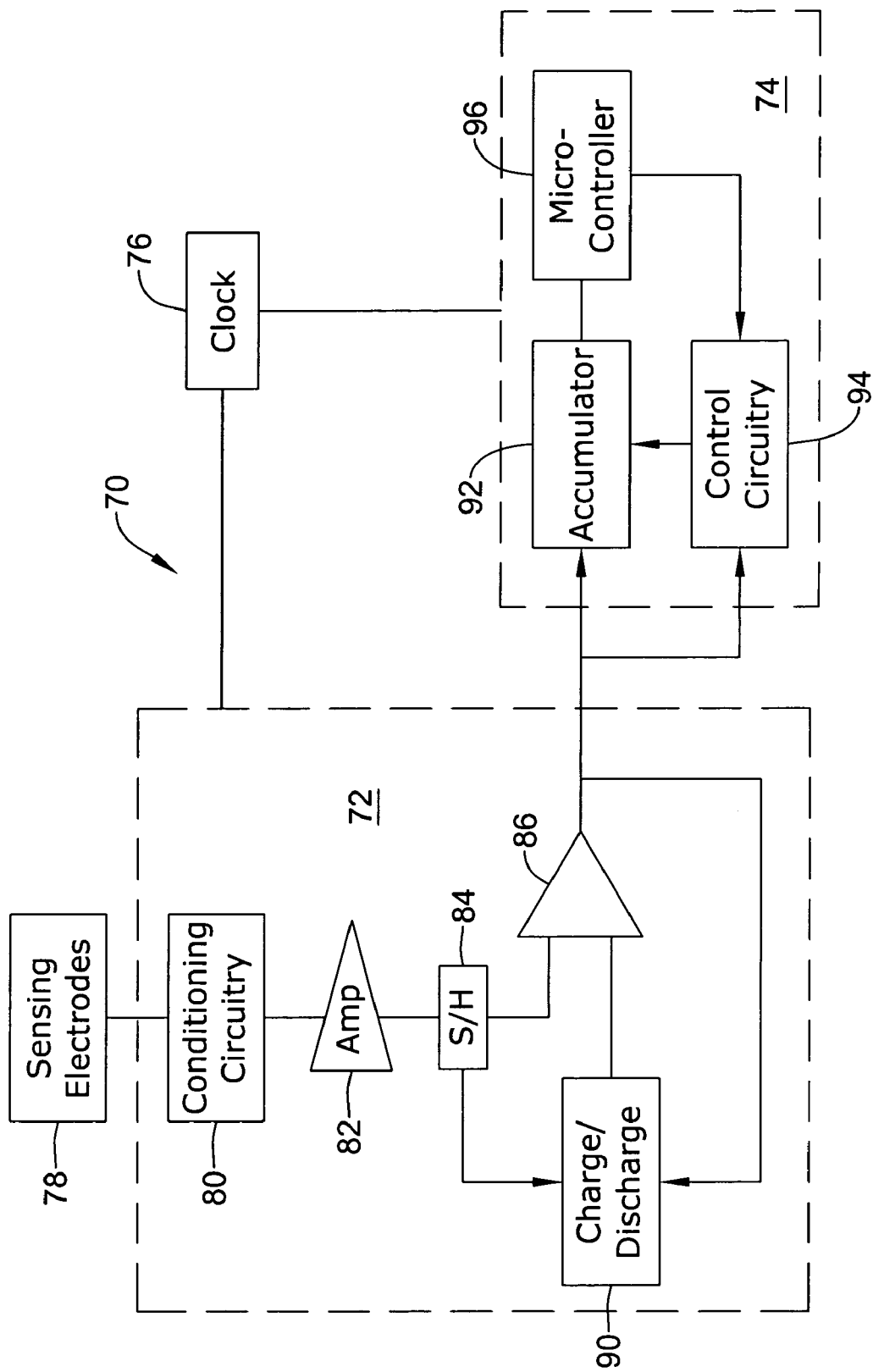
FIG. 4A illustrates a first signal analysis system.

Some embodiments of the present invention are adapted for use with an analog-to-digital converter (ADC) similar to that illustrated in commonly assigned U.S. Pat. No. 6,927,721, entitled LOW POWER A/D CONVERTER, the disclosure of which is incorporated herein by reference. FIG. 4A illustrates an example of a non-conventional ADC as part of analysis system 70. The illustrative analysis system 70 includes an analog chip 72 and digital chip 74. A clock 76 is also shown and may be provided on either chip or, as shown, may be separately provided. The clock 76 may allow synchronization of certain processes on each chip 72, 74.

Sensing electrodes 78 capture an electrical signal from implanted positions in a patient. The electrical signal is received by conditioning circuitry 80 (such as DC-blocking capacitors and other filtering devices, pull-up or pull-down resistors, switching circuitry allowing for selection and/or blanking of appropriate sensing vectors, and other suitable circuitry) and supplied to an amplifier 82. The amplifier 82 provides an output to sample and hold (S/H) circuitry 84. The S/H circuitry 84 provides an output to one input of a comparator 86. The other input for the comparator 86 is coupled to charge/discharge circuitry 90.

The charge/discharge circuitry 90 may include, for example, a comparator providing an output to a capacitor via a resistor such that the input to the comparator 86 is the voltage that is stored on the capacitor. In another embodiment, the charge/discharge circuitry includes a digital-to-analog converter (DAC) and an associated up/down counter such that the output of the DAC is controlled by the output of the counter, wherein the counter counts up or down depending on whether the output of the comparator 86 is high or low after each new sample occurs. Once the output of the comparator 86 switches, the charge/discharge circuitry 90 latches to hold its output stable until a next sample is indicated by the S/H circuitry 84.

When a new sample is received by the S/H 84, a latch in the charge/discharge circuitry 90 is set/reset, and the output of the comparator 86 is used to determine whether the new sample has a greater or lesser voltage than the previous voltage. If the new sample has a higher voltage, the output of the comparator 86 goes high, causing the charge/discharge circuitry 90 to increase the voltage it supplies to the comparator 86 until it equals the new sample. At this time, the output of the comparator 86 switches, indicating to the charge/discharge circuitry 90 that charging/discharging is to stop. If the new sample has a lower voltage, the output of the comparator 86 goes low, causing the charge/discharge circuitry 90 to perform the reverse steps. Again, the output of the comparator 86 switches, indicating to the charge/discharge circuitry 90 that charging/discharging is to stop.

The digital chip 74 includes an accumulator 92, control circuitry 94, and a microcontroller 96. The control circuitry 94 may be synchronized with the S/H 84 in an appropriate manner. For example, both may receive a signal from the microcontroller 96 indicating a new sample is to be taken. The control circuitry 94, when a new sample is supplied by S/H 84 to comparator 86, determines whether the output of the comparator 86 is high or low. If the comparator 86 output is high, the control circuitry 94 causes the accumulator 92 to increment its stored value until the comparator 86 output switches. If the comparator 86 output is low, the control circuitry 94 causes the accumulator 92 to decrement its stored value until the comparator 86 output switches.

One or both of the speed of the charge/discharge circuitry 90 and/or the speed at which the comparator 86 counts up or down can be slew-rate limiting for this ADC. Rather than direct measurement of the received signal, this ADC provides an output determined by the relative change in the input from one sample to the next. Thus there may be uncertainty in the output when saturation occurs and/or when the input voltage changes in excess of the slew rate. In particular, referring back to FIG. 2, the ADC may not return to the original quiescent point $Q_4$ following saturation 54. A heuristic filter that adjusts the ADC accumulator toward a single quiescent point removes this variability.

Figure 4B:
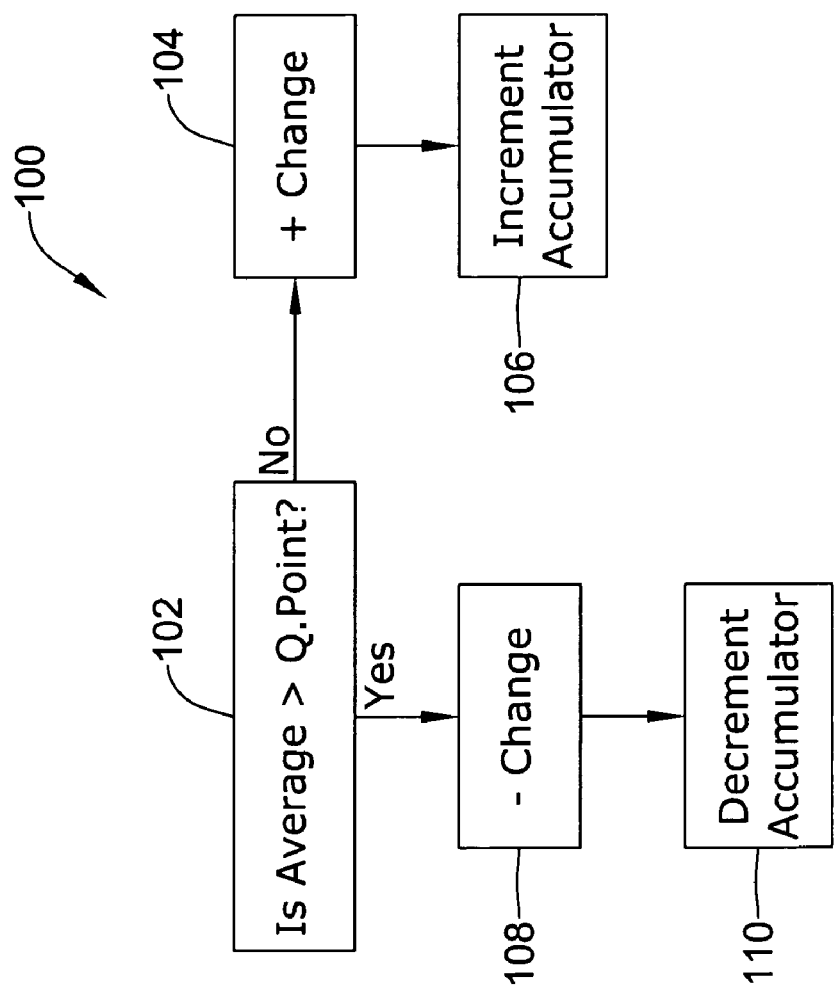
FIG. 4B is a block diagram illustrating a method of heuristic filtering for the signal analysis system of FIG. 4A.

FIG. 4B illustrates a method of operating a heuristic filter in association with the ADC shown in FIG. 4A. The method 100 first compares a value to the variable Q.Point, as shown at 102. This comparison at 100 may be a simple comparison of a most recent sample to the Q.Point. Alternatively, and as shown in FIG. 4B, some methods use a different value, "Average," which may be the average of a previous number of digital signal samples. Any appropriate number of samples may be selected. In an illustrative example, 25 previous samples may be averaged in a system taking samples at 256 Hz, spanning a period of about 100 milliseconds, which may be long enough to span any cardiac or noise event. An "average" of only the most recent signal would also include an embodiment in which only a single sample is considered.

In the illustrative embodiment, Q.Point is a desired quiescent point for the accumulator or ADC. Q.Point may be at or near the center of the dynamic range of the accumulator. In an illustrative example, a 9-bit accumulator is used and 256, the center of the accumulator range, is selected as the Q.Point. Other accumulator sizes may be used. Also, an off-center quiescent point may also be chosen, as shown below in FIG. 20.

If the Average is equal to or below the Q.Point, a positive change is indicated, as shown at 104, and the accumulator is incremented as shown at 106. Otherwise, a negative change is indicated, as shown at 108, and the accumulator is decremented, as shown at 110.

In an illustrative example, the heuristic filter can be either enabled or disabled, and it is called periodically. For example, the heuristic filter may operate at 16 Hz, giving a periodicity of 62.5 milliseconds. In this manner, when the heuristic filter is enabled, each time it is called, it moves the accumulator either up or down depending on whether the previous Average of the accumulator is less than or greater than the quiescent point. If operating at 16 Hz, the heuristic filter would be called 16 times per second. If the ADC is operating away from the desired quiescent point, the heuristic filter will repeatedly move the accumulator toward the quiescent point. If the ADC is away from the quiescent point due to normal R-wave fluctuations, the heuristic filter may cause the ADC output to overshoot somewhat when the ADC returns to the quiescent point.

A later example will illustrate a dynamic heuristic filter in which the frequency or periodicity of the heuristic filter is changed as well.

Figure 5A:
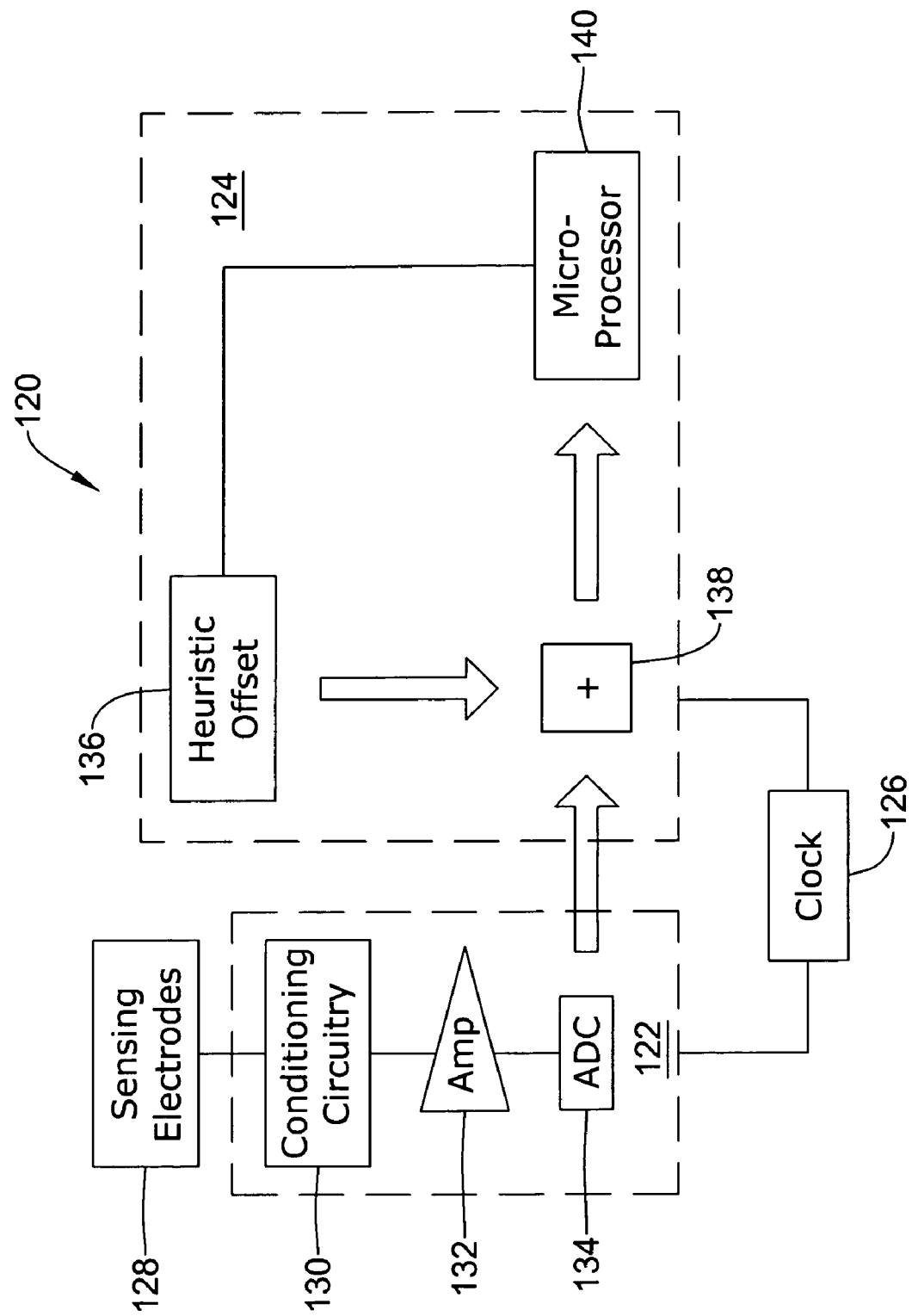
FIG. 5A illustrates a second signal analysis system.

FIG. 5A illustrates a second signal analysis system. The system 120 includes an analog chip 122 and a digital chip 124, as well as a clock 126 that may be on either chip 122, 124 or may be separately provided. A signal is captured from implanted sensing electrodes 128 using conditioning circuitry 130, which may be similar to that shown in FIG. 4A. The signal then goes to an amplifier 132, which feeds an output to ADC 134 (an S/H sub-circuit may also be included, or the ADC may be a latched or gated ADC). The ADC 134 may be a successive approximation ADC or any other suitable ADC. The ADC 134 provides a signal to the digital chip 124.

The digital chip 124 includes heuristic offset circuitry 136, an adder 138, and a microprocessor 140. The heuristic offset circuitry 136 may be a register/accumulator that stores a value (the heuristic offset) used to offset the output of the ADC toward a desired quiescent point. Thus, the adder 138 adds the output of the ADC and the heuristic offset circuitry 136, and provides the result to the microprocessor 140.

Figure 5B:
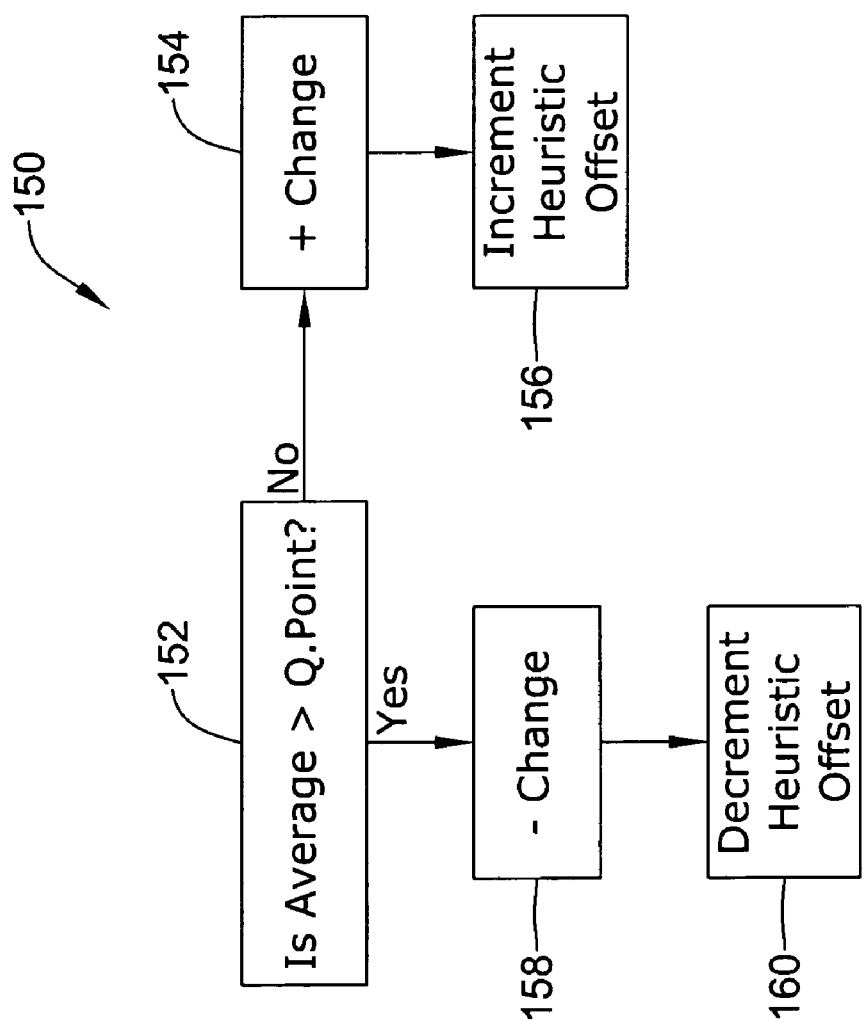
FIG. 5B is a block diagram illustrating a method of heuristic filtering using a heuristic offset for the signal analysis system of FIG. 5A.

FIG. 5B is a block diagram illustrating a method of heuristic filtering using a heuristic offset for the system of FIG. 5A. The method 150 first determines whether a value "Average" is greater than a variable "Q.point". Again, if desired, the "Average" may cover any suitable number of samples, or may be replaced by a single value from a most recent sample. The Q.Point, as before, is a desired quiescent point. If the Average is equal to or less than the Q.Point, a positive change is indicated, as shown at 154, and the heuristic offset is incremented, as shown at 156. This pushes the sum from adder 138 (FIG. 5A) up in value. If, instead, the Average is above the Q.Point at 152, a negative change is indicated, as shown at 158, and the heuristic offset is decremented, as shown at 160. Because the output of the ADC in FIG. 5A is direct, rather than indirect as in FIG. 4A, an offset is used, rather than an adjustment to the ADC itself. The offset may also be used in association with the device of FIG. 4A.

The method 100 may be executed by the control circuitry 94 or the microcontroller 96 (FIG. 4A), which may direct the accumulator 92 to increment or decrement, for example. In another example, the system of FIG. 4A may instead use a heuristic offset (FIGS. 5A-5B), which can be maintained and calculated internal to the microcontroller 96. In yet another example, the accumulator 92 may itself be incorporated into the microcontroller 96, which may perform the method 100 internally or may instead perform a method using a heuristic offset (FIGS. 5A-5B).

Figure 6:
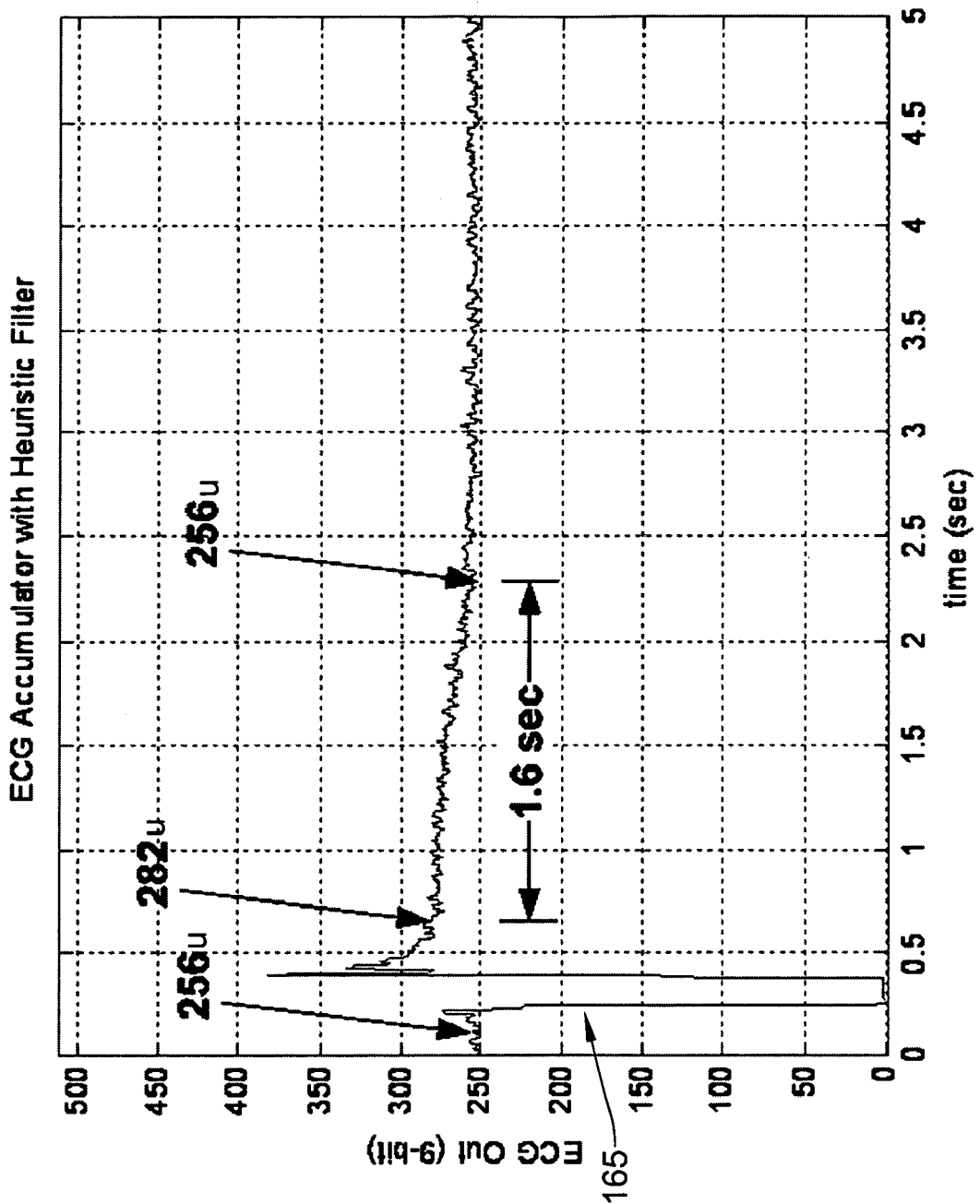
FIG. 6 is a graphical example of an ECG accumulator output with heuristic filtering applied.

FIG. 6 illustrates ECG analysis using heuristic filtering. The illustrative example follows the model of FIG. 4A, with an accumulator holding an ADC output value on the digital chip. A 9-bit accumulator is assumed, with a dynamic range as shown of 0-512 units. A shock is delivered at 165, causing saturation of the system inputs.

Prior to shock delivery 165, the average, over time, of the accumulator output was 256 units, as indicated. However, after shock delivery 165, the system recovers to an average of about 282 units. The heuristic filter, operating at 16 Hz, returns the system to an average of 256 units. In the illustrative example, the system takes about 1.6 seconds to recover from 282 units to 256 units.

Figure 7:
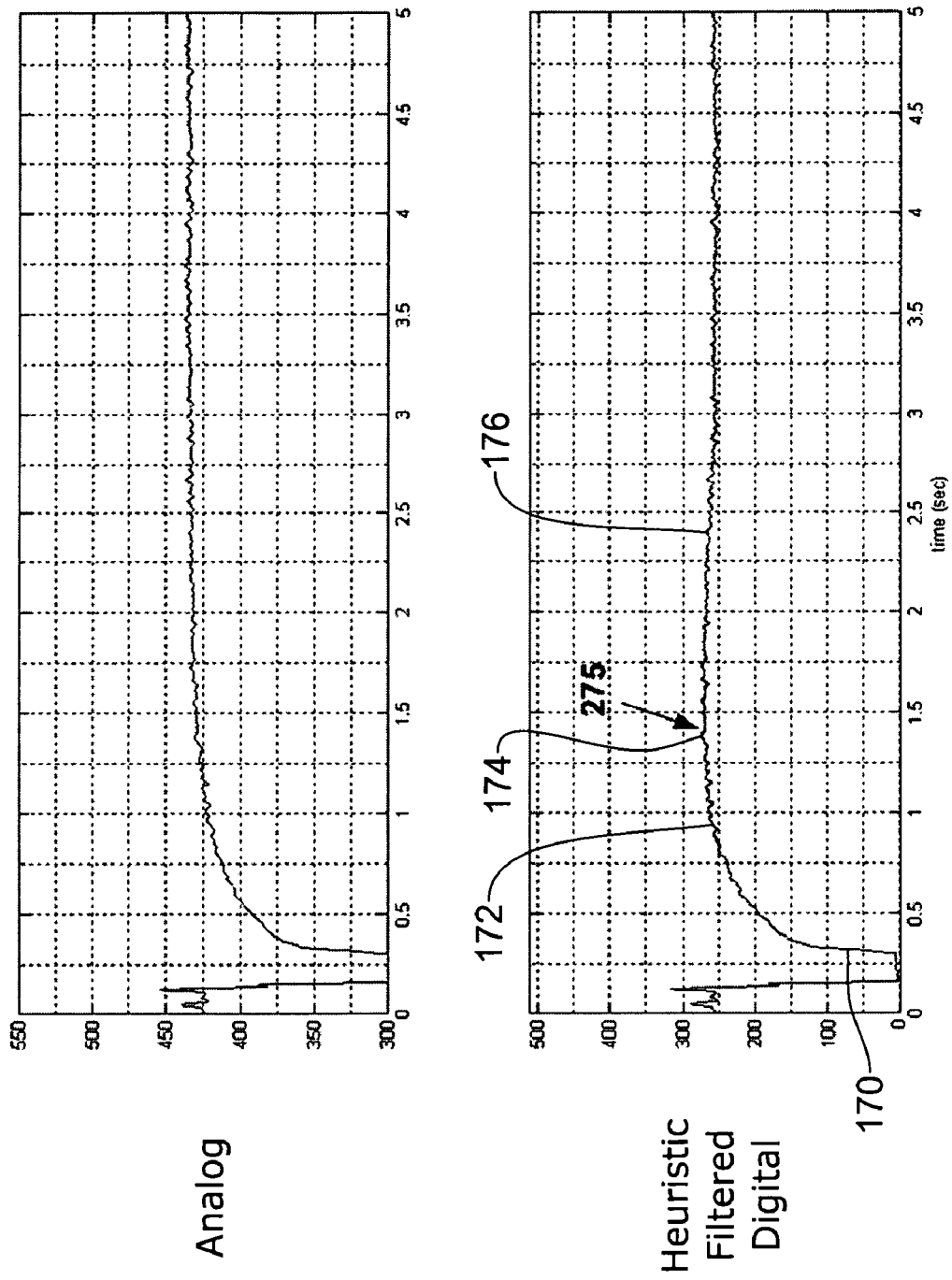
FIG. 7 compares an analog ECG signal to a corresponding digital signal after heuristic filtering.

FIG. 7 compares an analog ECG signal to a corresponding ECG circuit output after heuristic filtering. In the illustrative example of FIG. 7, the system undergoes a shock at about t=0.1 seconds. As indicated in the analog signal graph, there is a slow recovery for the analog signal to a relatively flat period starting at about 1.5 seconds.

The lower graph indicates a Heuristic-filtered digital signal. After the shock, the digital signal initially recovers more quickly, as shown at 170. By the time indicated at 172, the heuristic filter and/or the ADC operation have returned to the center point of the 9-bit output. However, the analog signal has not recovered to its fully relaxed state, and the continuing rise of the analog signal pushes the digital signal above the quiescent point. Further, at time 172, if an "Average" of previous values is used to make the heuristic filter determination of whether to increment or decrement the ADC accumulator (or increase or decrease the heuristic offset), the heuristic filter will also contribute to overshoot as shown at 174. After the overshoot peaks at 274 units, as indicated, the system then recovers, as shown at 176, to relatively steady state.

To prevent the overshoot shown in FIG. 7, some illustrative examples further include a dynamic heuristic filter in which the frequency of the heuristic filter changes as the quiescent point is approached.

Figure 8:
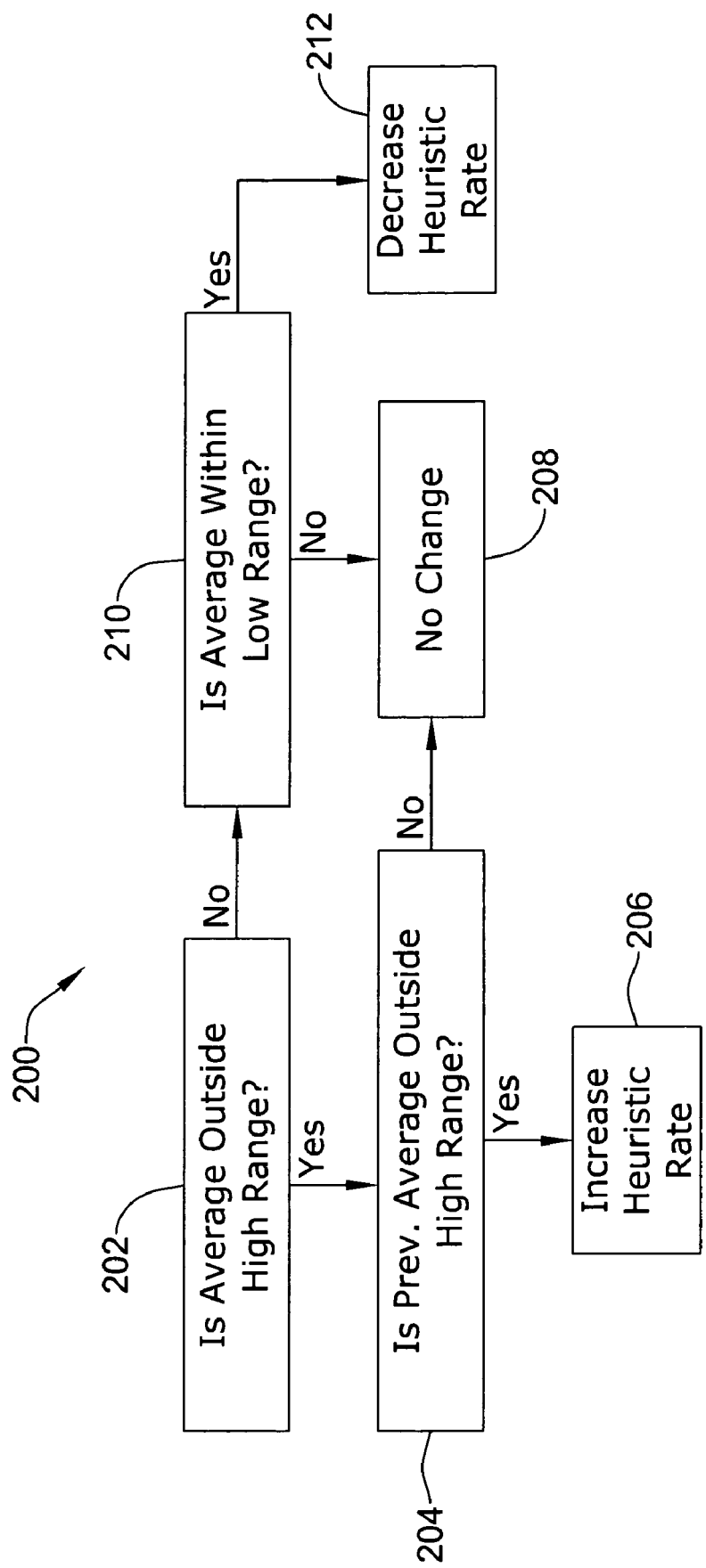
FIG. 8 is a block diagram for an illustrative method of dynamic heuristic filtering.

FIG. 8 is a block diagram showing operation of an illustrative heuristic filter. The method 200 begins by comparing the Average of N previous sample amplitudes (or magnitudes, if desired) to a predetermined High Range variable, as shown at 202. The number N of samples used in the Average for this stage may be selected to span a typical R-wave, for example, at 256 Hz, 25 samples would represent 100 ms of signal, wide enough to span most R-waves. The High Range variable determines whether the Average is far enough away from the desired quiescent point that an increase toward the maximum heuristic filter rate is desirable. If the Average is outside the High Range at 202, the method continues to 204 and determines whether the Previous Average was also outside the High Range. If so, then the heuristic rate is increased, as shown at 206. Two checks are taken before an increase in the heuristic rate in this illustrative example; if desired, a single check may be performed. The double check makes the heuristic filtering more conservative, while still allowing recovery when the Average fails to return toward the quiescent point.

In an illustrative example, the heuristic rate is scaled from 0 to 7 as follows:

| Heuristic Filtering Level | Actual Rate (Hz) |
| --- | --- |
| 0 | 8 |
| 1 | 16 |
| 2 | 32 |
| 3 | 64 |
| 4 | 128 |
| 5 | 256 |
| 6 | 512 |
| 7 | 1024 |

Different scales may be used, as desired. If, for example, the heuristic filtering is operating at level 4, then the heuristic filter is called at a rate of 128 Hz, or every 7.8 ms. Supposing a 9-bit accumulator and a desired quiescent point of 256 digital units, a High Range could be 240-272. Then, if the Average=232, and previous Average=231, the heuristic filtering would be changed to level 5 at step 206, increasing the rate to 256 Hz. This example uses a relatively wide High Range. Another illustrative example uses a narrower High Range, such that for a 9-bit accumulator having a desired quiescent point of 256 digital units, the illustrative example has a High Range of 252-260 digital units. If a larger accumulator were used (such as a 12-bit accumulator), the range of available frequencies may be increased.

If the double check at 204 fails, then no change occurs, as shown at 208. If the Average is not outside the High Range at 202, then it is determined whether the Average is within the Low Range, as shown at 210. If so, then the Heuristic Rate is decreased, as shown at 212. Again supposing a 9-bit accumulator and a desired quiescent point of 256 digital units, a Low Range could be 254-258 digital units. If the heuristic filtering is operating at level 4 and the Average=255 digital units, the method would reach step 212 and decrease the heuristic filtering to level 3. A wider or narrower Low Range may also be used. If the Average is not within the Low Range at 210, then no change occurs, as shown at 208.

Figure 9:
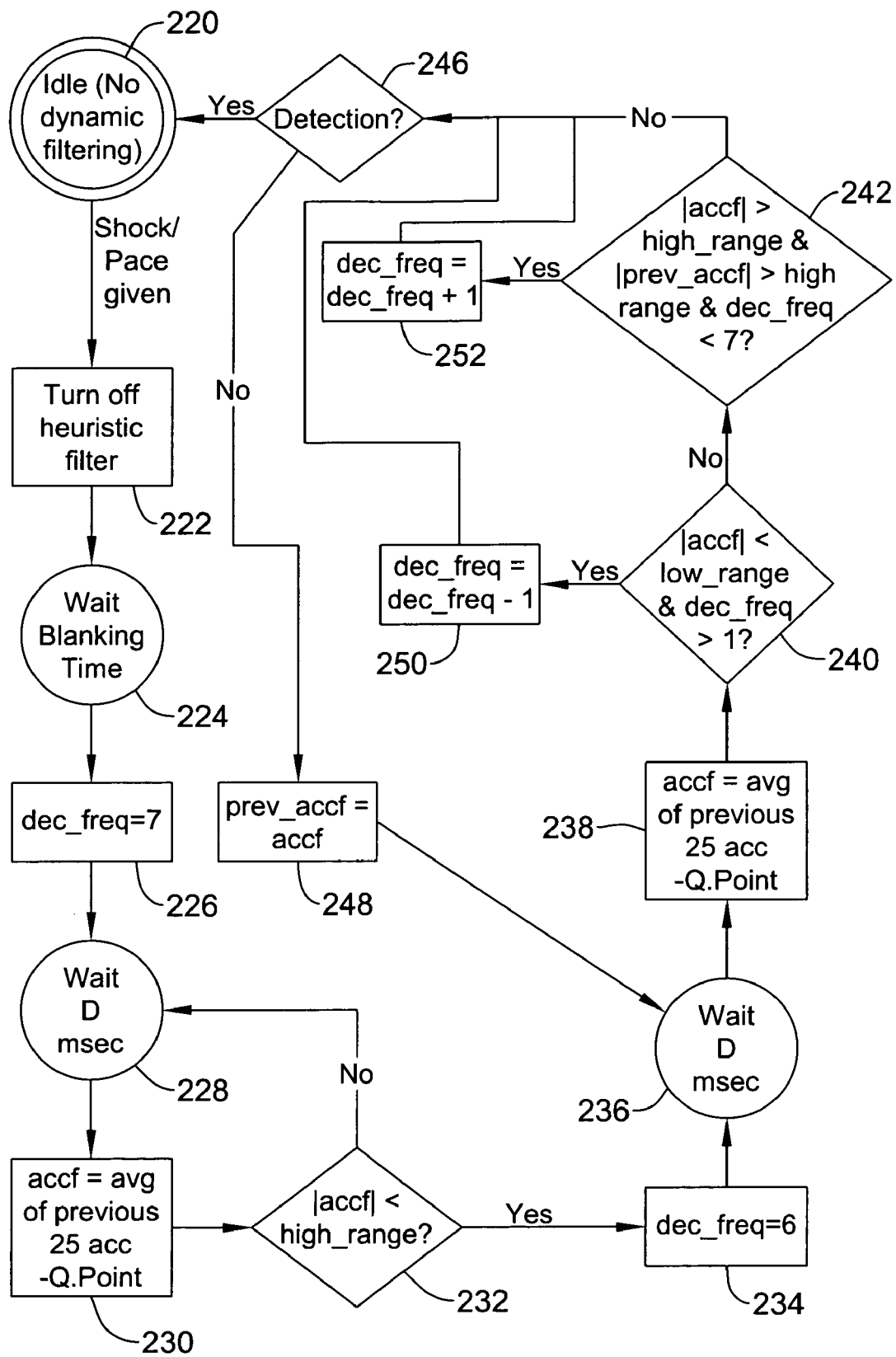
FIG. 9 is a block diagram for an illustrative method of dynamic heuristic filtering.

FIG. 9 is a block diagram for a method of dynamic heuristic filtering. The method illustrated in FIG. 9 provides a detailed illustration that applies the method of FIG. 8 to a system such as that shown in FIGS. 4A-4B. The method in FIG. 9 includes an Idle block, as illustrated at 220, during which there is no dynamic heuristic filtering occur. After a shock or pace is given, the method goes to step 222, wherein the heuristic filter is turned off as the shock is given and during a blanking period that follows the shock, as indicated at 224. Next, a variable dec_freq is set to 7, as shown at 226. Dec-freq is a variable indicating the state or frequency of the heuristic filter. In the illustrative embodiment, the above table of heuristic filter frequencies is used, with setting 7 being the highest frequency of operation. In the example, step 226 sets the dynamic heuristic filter to its highest frequency following the blanking time after a shock is delivered.

The method then enters a loop comprising steps 228, 230, 232. The wait state 228 occurs for a predetermined time period. The illustrative analyses shown below in FIGS. 10-19 A-C alternate between D=50 ms and D=100 ms and show that the selection of one or the other may affect the output. As shown at 230, a variable accf is set to the average of the previous 25 accumulator values (the previous sampled signal amplitudes), less the desired quiescent point. Thus, accf provides the difference between the average of the sampled signal and the desired quiescent point. Next, the absolute value of accf is compared to a variable, high_range, as shown at 232. In an illustrative example, a 9-bit accumulator is used, with a centered quiescent point at 256 digital units, and high_range is set to 4. Different sizes and ranges may be used, and the quiescent point need not be centered on the digital scale, although it often will be.

The loop of steps 228, 230, 232 continues until accf falls within high_range and the condition at 232 is met. The method then reduces the frequency of the heuristic filter by setting dec_freq=6, as shown at 234. The method then enters another loop including steps 236, 238, 240, 242, 246, 248, 250, and 252.

The second loop begins with a wait state 236 which, as with step 228 occurs for a predetermined period of time such as 50 ms or 100 ms, although other values may also be used. Next, accf is calculated, as before, as shown at 238. Then, as shown at 240, the absolute value of accf is compared to a variable, low_range, and it is determined whether dec_freq is greater than one. The variable low_range is set to 2 in an illustrative embodiment. In the illustrative example, the lowest value that dec_freq can have is 1, thus the second condition on step 240. If either condition fails at 240, the method continues to step 242.

At step 242, the absolute value of accf is compared to high_range, the absolute value of the previous accf is compared to high_range, and it is determined whether dec_freq is less than 7. As before in FIG. 8, both the present and previous values of accf must fall outside of the high range to trigger an increase in dec_freq. Also, the maximum value for dec_freq in this illustrative example is 7. The double-check of accf and previous accf may be omitted, and a single check of accf may be performed instead. The specific range/values for dec_freq may also vary in additional embodiments. Again, if either condition fails at 242, the method continues to step 246.

In step 246, it is determined whether a detection has occurred. If a detection has occurred, the dynamic heuristic filter is disabled and the method returns to the idle state at 220. Otherwise, the method continues to step 248 where the previous accf value is updated to the most recently calculated accf. The method then returns to the wait state at 236 and waits for the next iteration. In another embodiment, a detection may trigger an interrupt that places the heuristic filter in the idle state 220.

Going back into the loop, if the conditions at 240 are both met, it is determined that the frequency of the heuristic filter may be lowered to avoid overshooting the quiescent point and limiting any resulting oscillation. Thus, as shown at 250, dec_freq is reduced by one. The method then goes to step 246 as before. If, instead, the conditions at 242 are met, it is determined that the detection architecture/hardware has moved away from the quiescent point sufficiently to justify increasing the frequency of the heuristic filter. Therefore, dec_freq is increased by one, and the method goes to step 246 as before. In this manner, the heuristic frequency is dynamically changed until a detection occurs.

In the example of FIG. 9, the variables high_range and low_range are considered thresholds for comparison to accf, which is a variable that is related to the amplitude of the detected cardiac signal that is received from implanted electrodes.

Figures 10A, 10B, 10C:
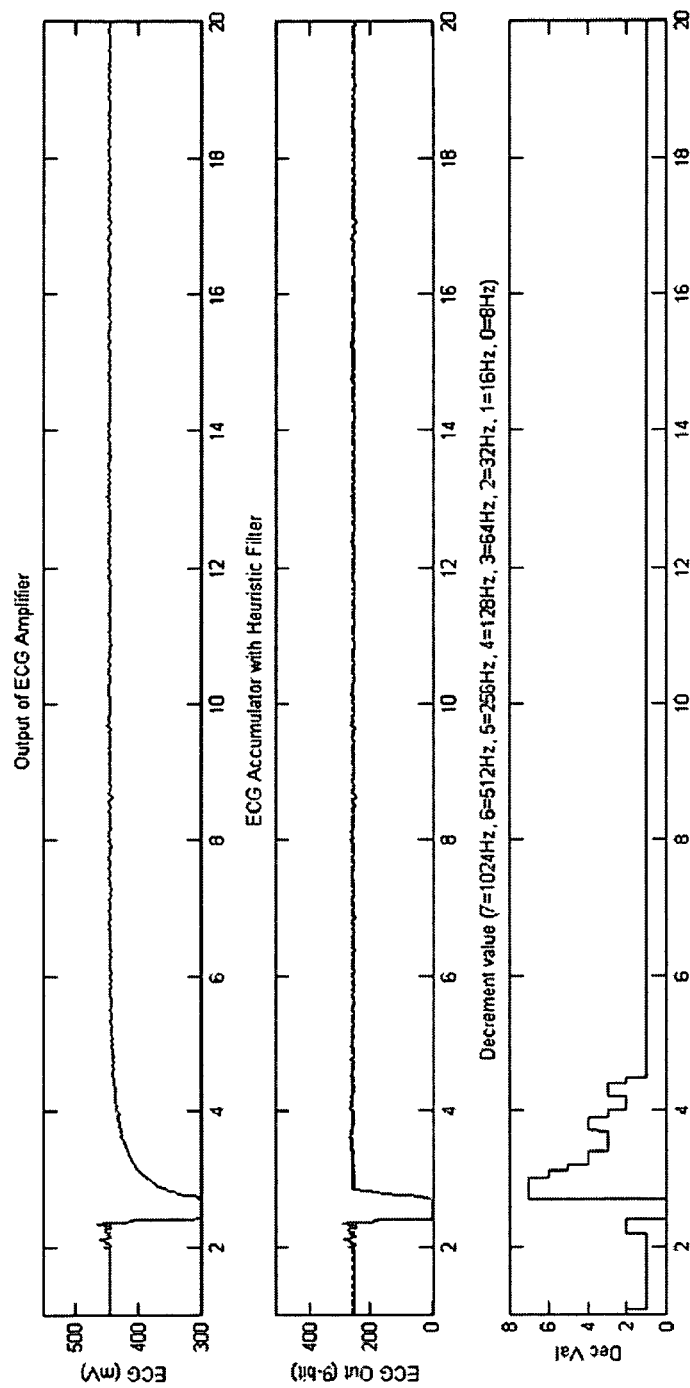
FIGS. 10A-10C, 11A-11C, 12A-12C, 13A-13C, 14A-14C and 15A-15C illustrate simulated analysis of cardiac signals following delivery of a shock, including analog ECG amplifier output, a digital representation of the cardiac signal, and the status of an associated heuristic filter.
Figures 11A, 11B, 11C:
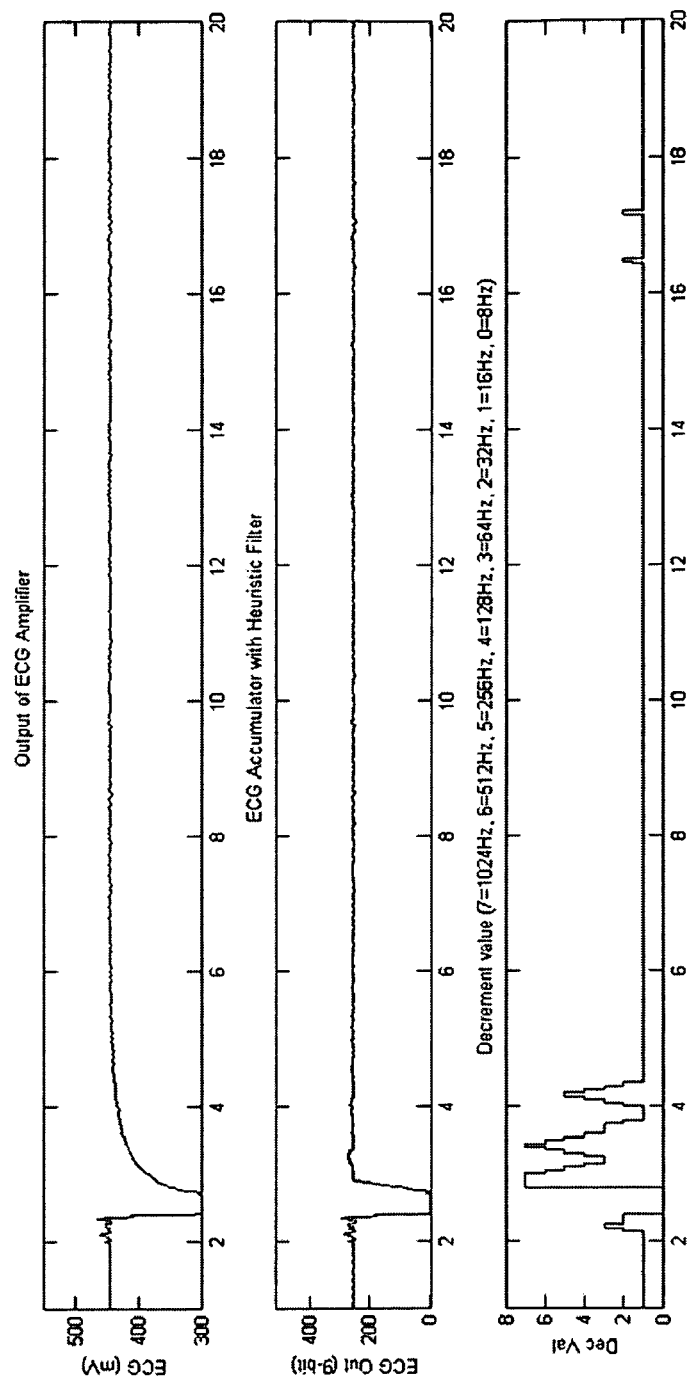
Figures 12A, 12B, 12C:
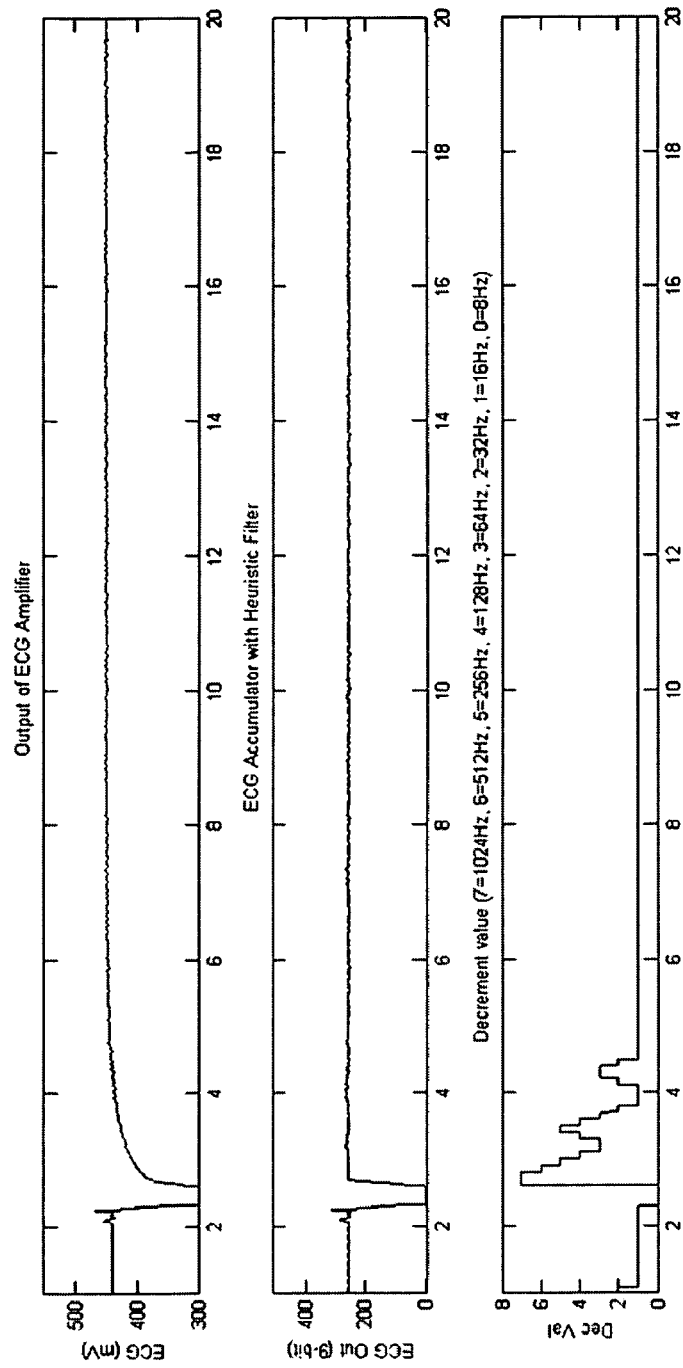

FIGS. 10A-10C, 11A-11C, 12A-12C, 13A-13C, 14A-14C and 15A-15C illustrate simulated analysis of cardiac signals following delivery of a shock, including analog ECG amplifier output, a digital representation of the cardiac signal, and the status of an associated heuristic filter. Each is based on a device using the ADC as shown in FIG. 4A. FIGS. 10A-10C, 12A-12C and 14A-14C each use D=100 ms, while FIGS. 11A-11C, 13A-13C and 15A-15C each use D=50 ms. The signal analyzed in FIGS. 10A-10C is the same as for 11A-11C, while the signal analyzed in FIGS. 12A-12C is the same as for 13A-13C, and the signal analyzed in FIGS. 14A-14C is the same as for 15A-15C.

FIG. 10A illustrates the output of the ECG amplifier, while FIG. 10B shows the output of the ECG accumulator, and FIG. 10C illustrates the state of the heuristic filter. It can be seen that the recovery, post shock, of the output of the ECG amplifier slopes up to a steady value (FIG. 10A), while the ECG accumulator provides a sharper output (FIG. 10B) and returns to a quiescent point much more quickly. The state of the heuristic filter includes some ringing as shown in FIG. 10C. While FIGS. 10A-10C use D=100 ms, using D=50 ms as shown in FIGS. 11A-11C causes the heuristic filter to reach dec_freq=1 more quickly, although a higher amplitude ringing occurs between approximately t=4.0 s and t=4.25 s.

Figures 13A, 13B, 13C:
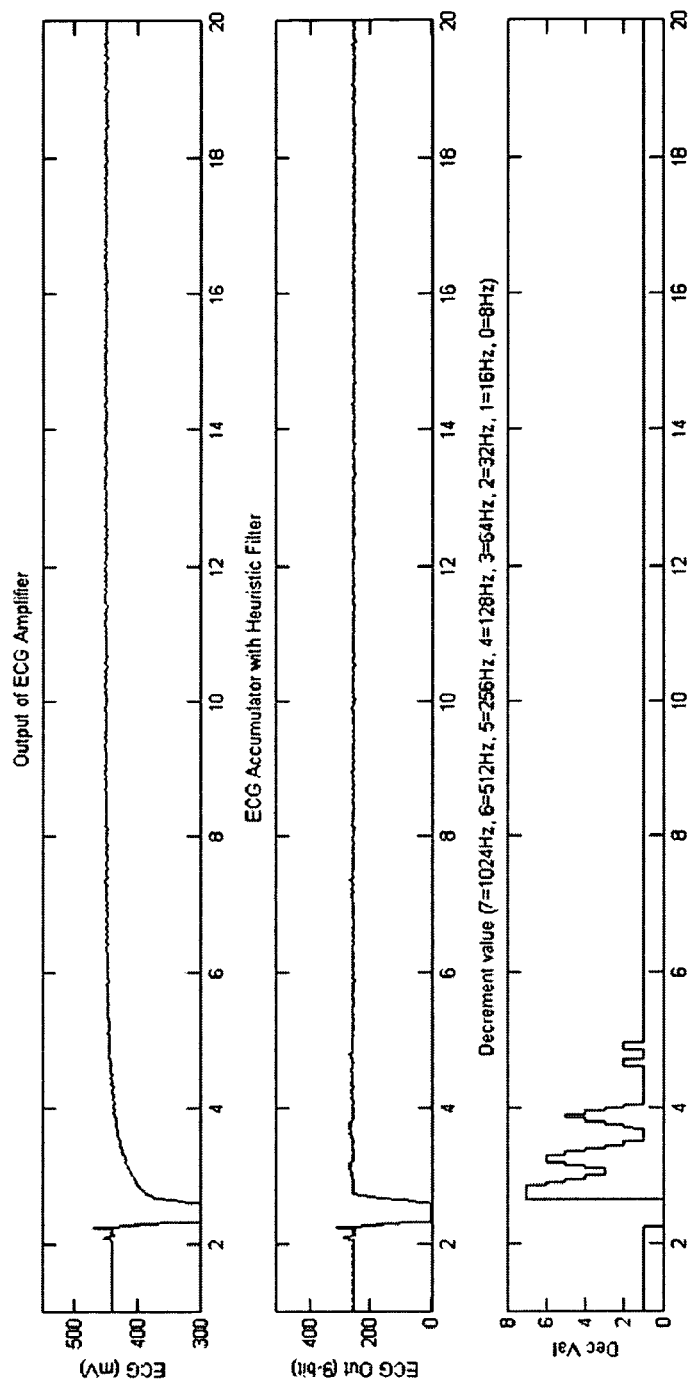
Figures 14A, 14B, 14C:
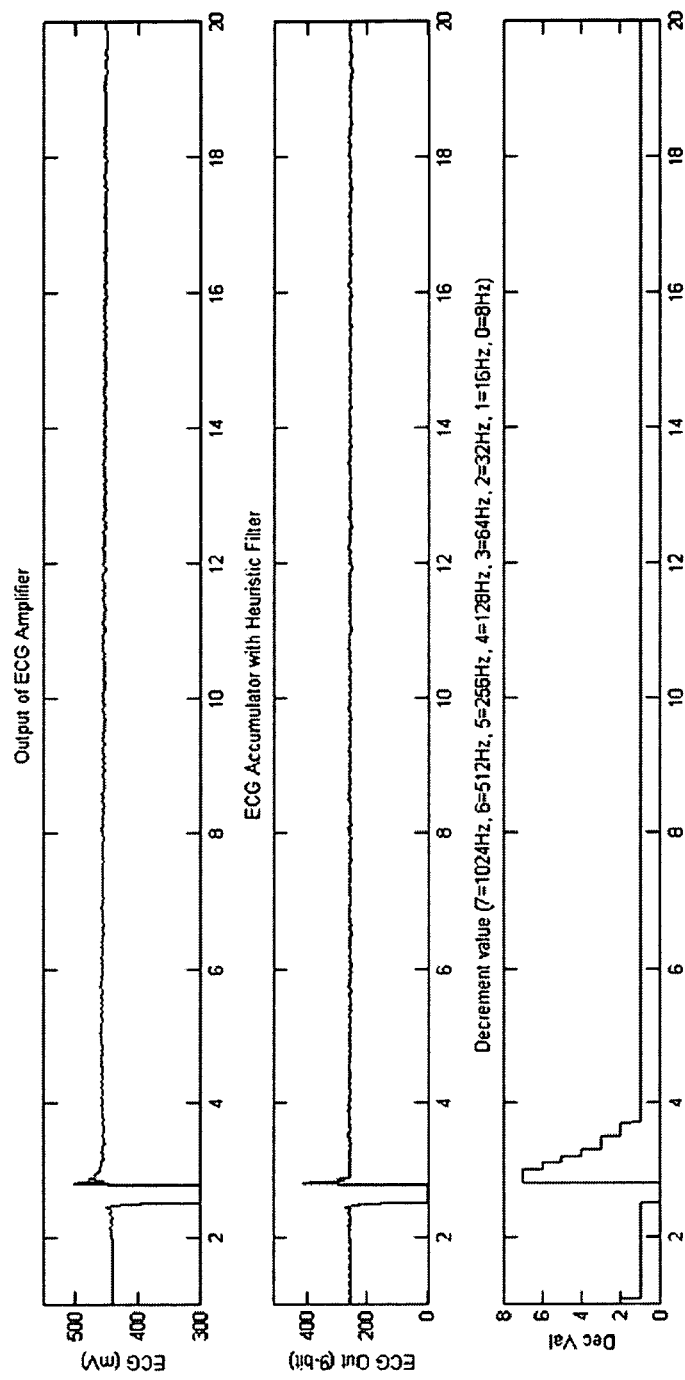

FIGS. 12A-12C show another example waveform and analysis with D=100 ms, while FIGS. 13A-13C show the same waveform with analysis at D=50 ms. More ringing can be observed than in the examples of FIGS. 10A-10C and 11A-11C. In each of the examples of FIGS. 10A-10C, 11A-11C, 12A-12C and 13A-13C, the ECG amplifier output gradually returns from a lower amplitude up to a settling point. It appears that the D=100 ms analysis performs more effectively for this waveform, as there is less ringing and the accumulator output is relatively flat.

Figures 15A, 15B, 15C:
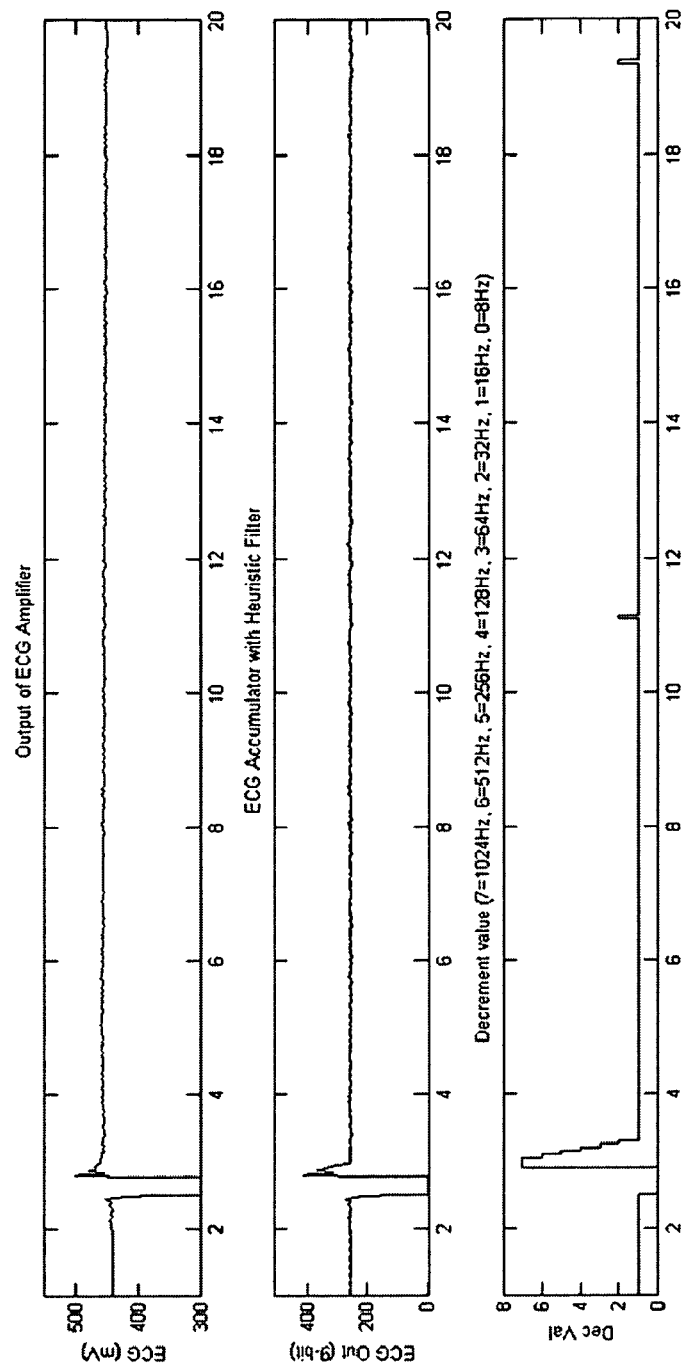

In contrast, the waveform of FIGS. 14A and 15A quickly returns to a higher amplitude than before the shock delivery and remains relatively flat after some initial ringing. For this waveform, as shown by FIGS. 14B-14C and 15B-15C, the lower D=50 ms analysis provides arguably better results by returning the filter to dec_freq=1 more quickly, although the accumulator signal does not settle as quickly as for the D=100 ms analysis.

While the simulations of FIGS. 10A-10C, 11A-11C, 12A-12C, 13A-13C, 14A-14C and 15A-15C appear to indicate that D=100 ms provides better performance, this may depend upon the waveform at issue as well as the particulars of the system under consideration, including amplifier and electrode gain/loss, sampling frequency, and other variables.

Figure 16A:
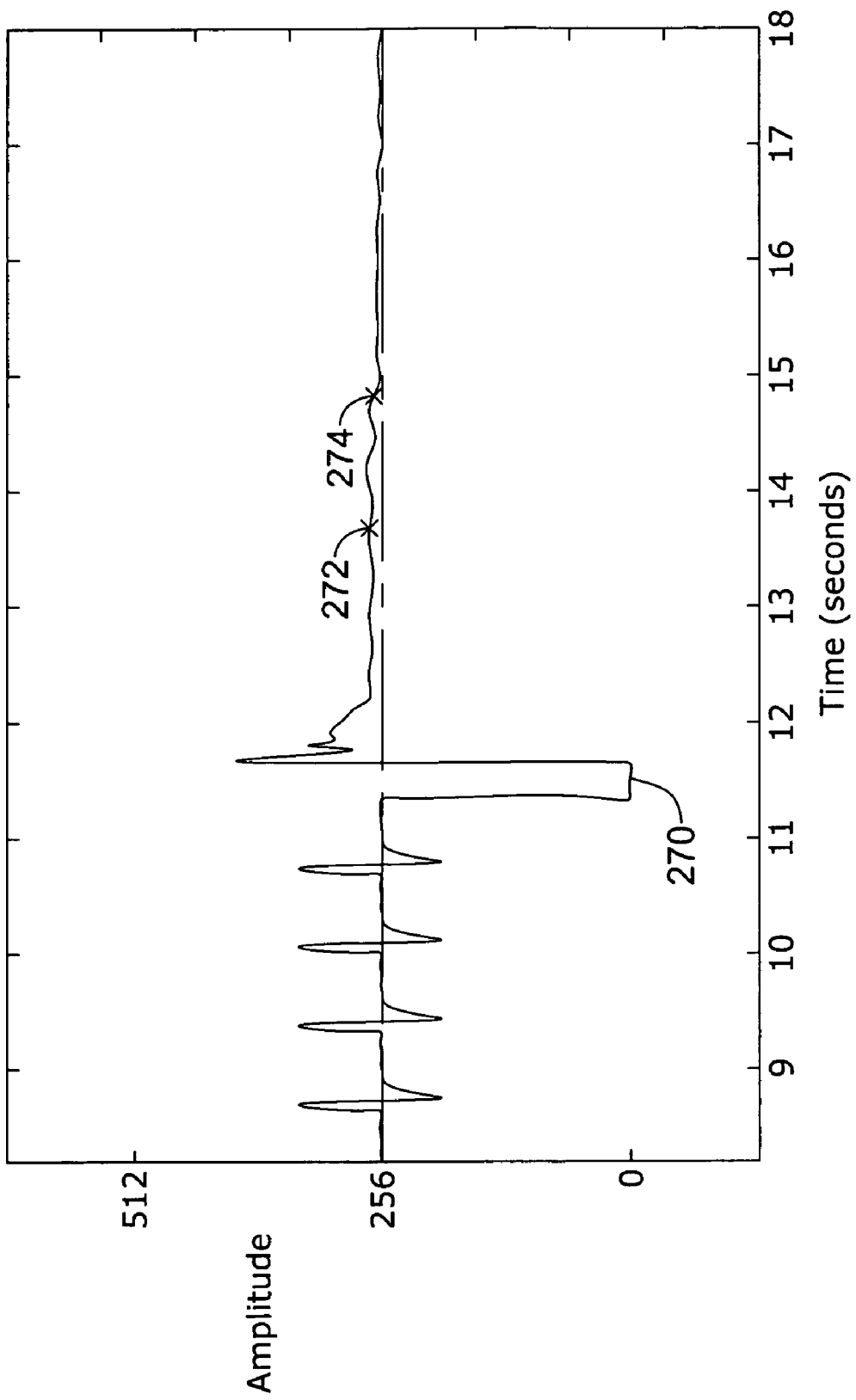
FIGS. 16A-16B, 17A-17B and 18A-18B compare analysis with and without heuristic filters applied for select simulated cardiac waveforms.

FIGS. 16A-16B, 17A-17B and 18A-18B compare analysis with and without heuristic filters applied for select simulated shocking waveforms. Referring to FIG. 16A, a simulated waveform was created by overlaying a normal sinus QRS signal onto a portion of a blank signal with a shock and recovery portion therein. The initial QRS allows for establishment of sensing parameters using a detection profile as shown above in FIG. 3. The QRS is applied for the four beats shown on the left, and terminates at about t=11 seconds. Thus, any detection occurring after the shock is applied at 270 is a false detection.

Figure 16B:
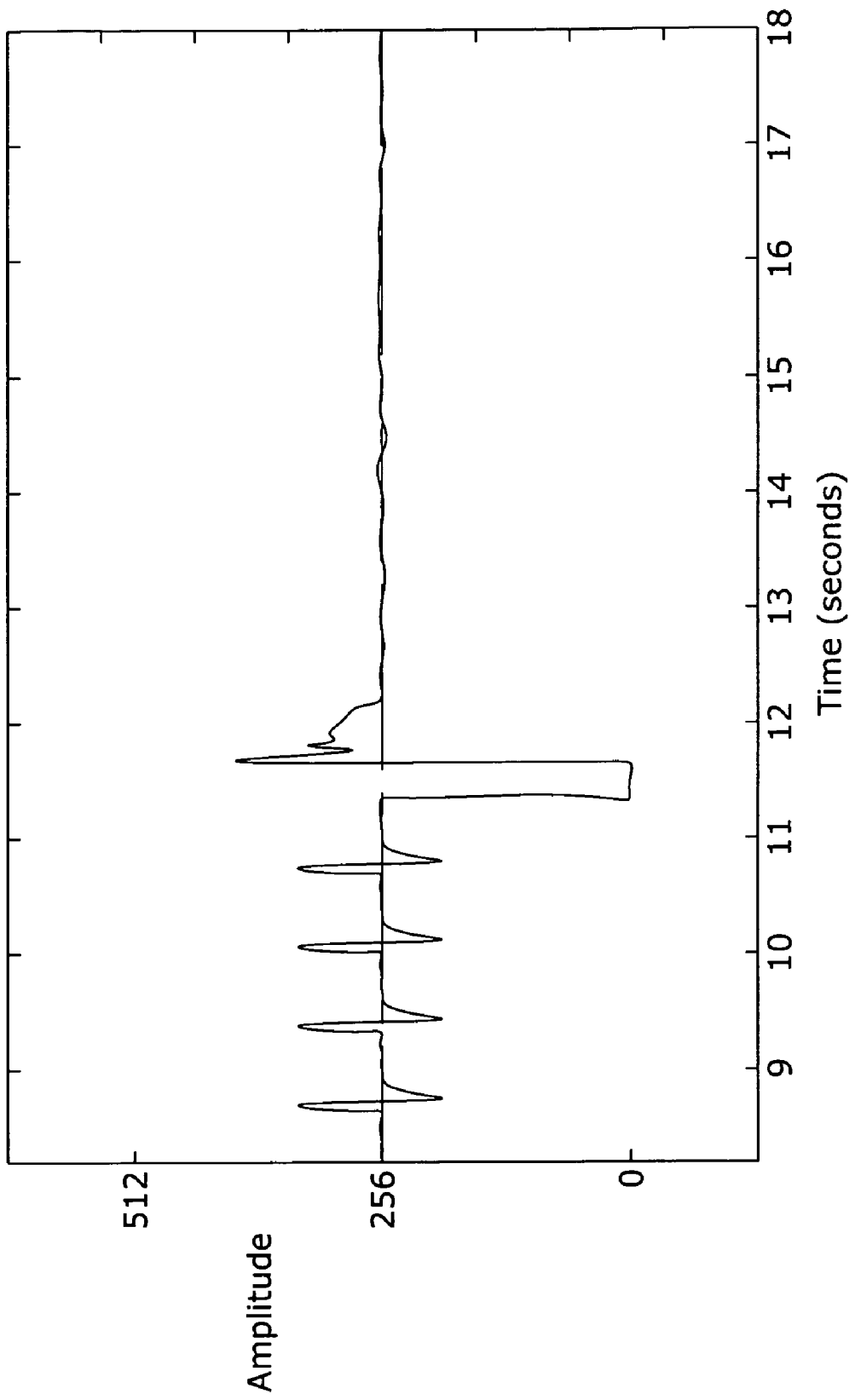

FIG. 16A illustrates analysis with the heuristic filter turned off. As can be seen, false detections occur at 272, 274. FIG. 16B, however, illustrates that the filtered signal is not only much flatter, returning to the quiescent point at about 256 ADC counts, but also, there are no false detections.

Figure 17A:
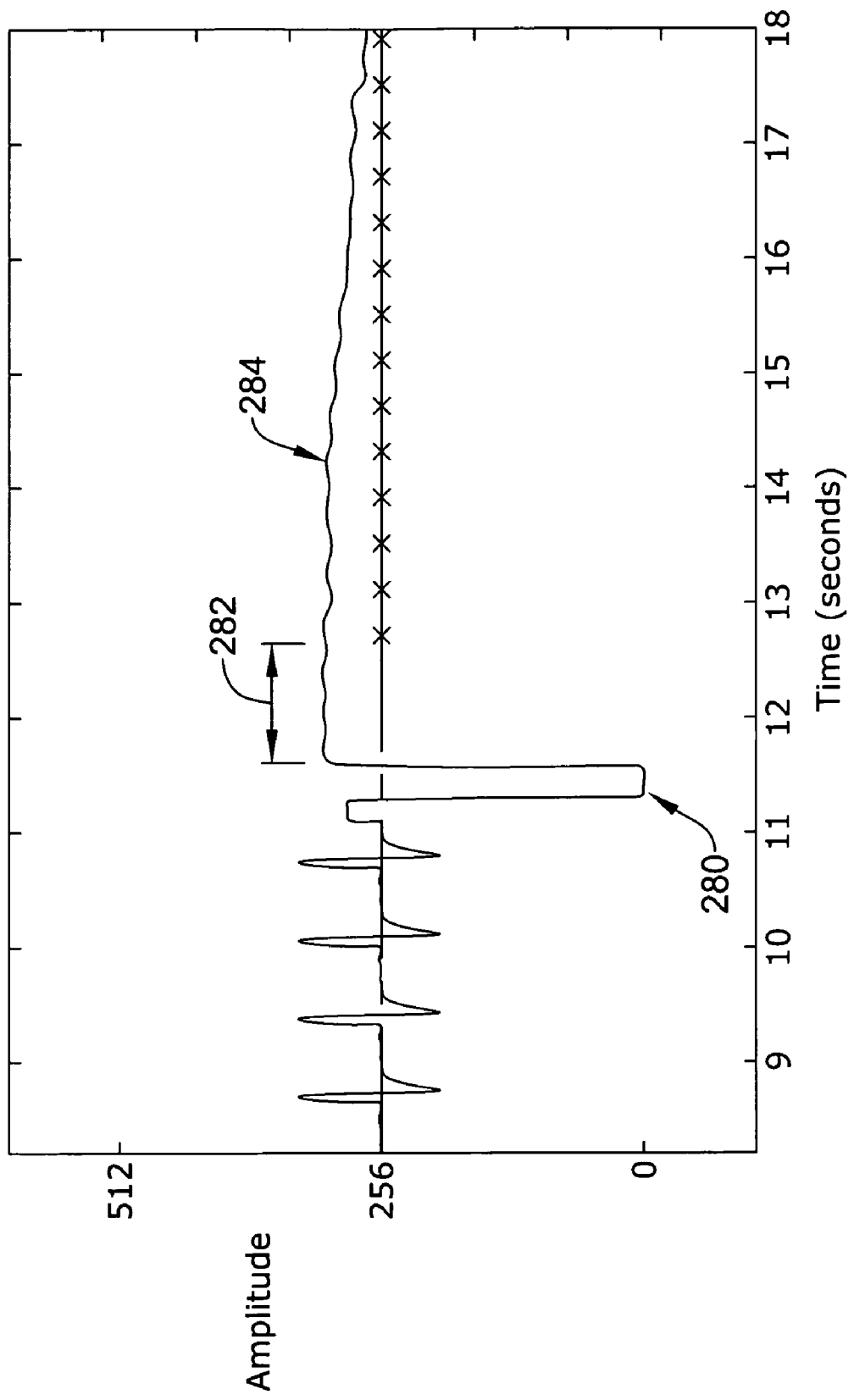
Figure 17B:
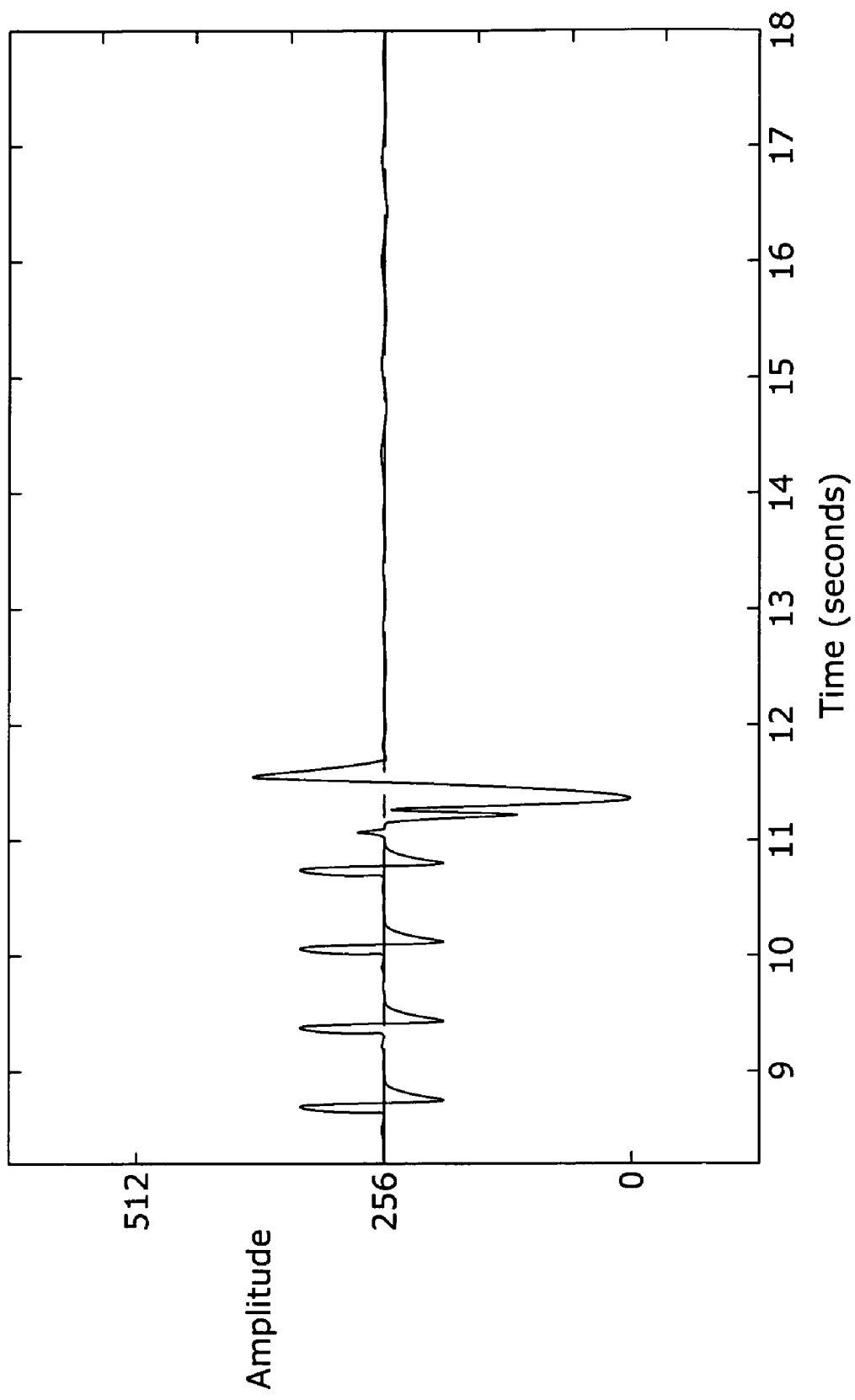

A similar approach was taken with FIGS. 17A-17B. The shock is applied at 280. A blanking period 282 occurs after the shock 280. In this instance, the after_shock signal remains relatively high for a long period of time, finally settling as t=17 and returning toward the quiescent point. The result is a large number of false detections indicated by the X's generally at 284. In contrast, FIG. 17B illustrates that the after_shock potential quickly returns to the quiescent value and remains there, averting the false detections.

Figure 18A:
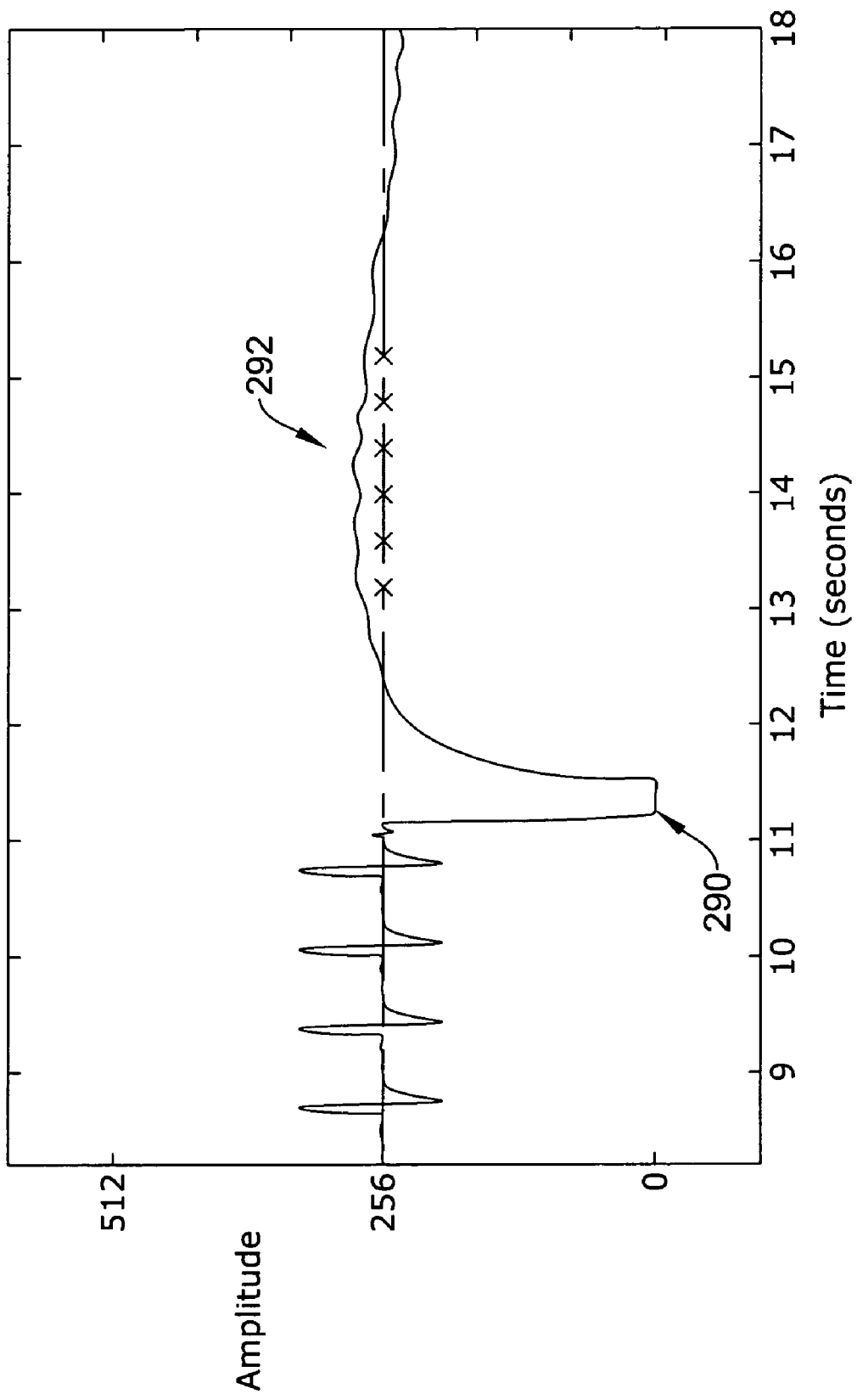
Figure 18B:
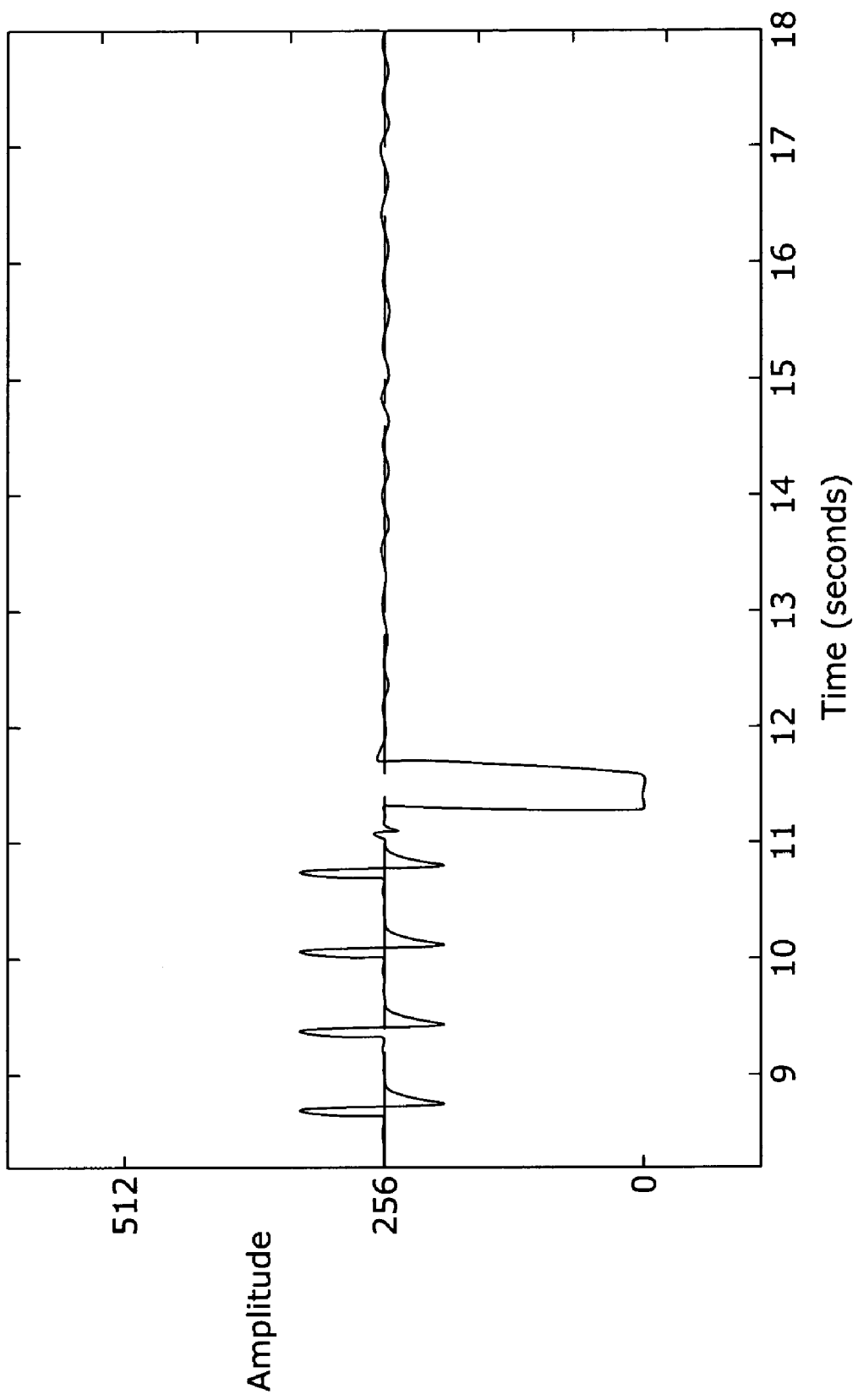

FIGS. 18A-18B again illustrate a recovery in which, without the heuristic filter in FIG. 18A, false detections 292 occur after a shock 290. These false detections are eliminated by the heuristic filter as shown in FIG. 18B.

Figure 19:
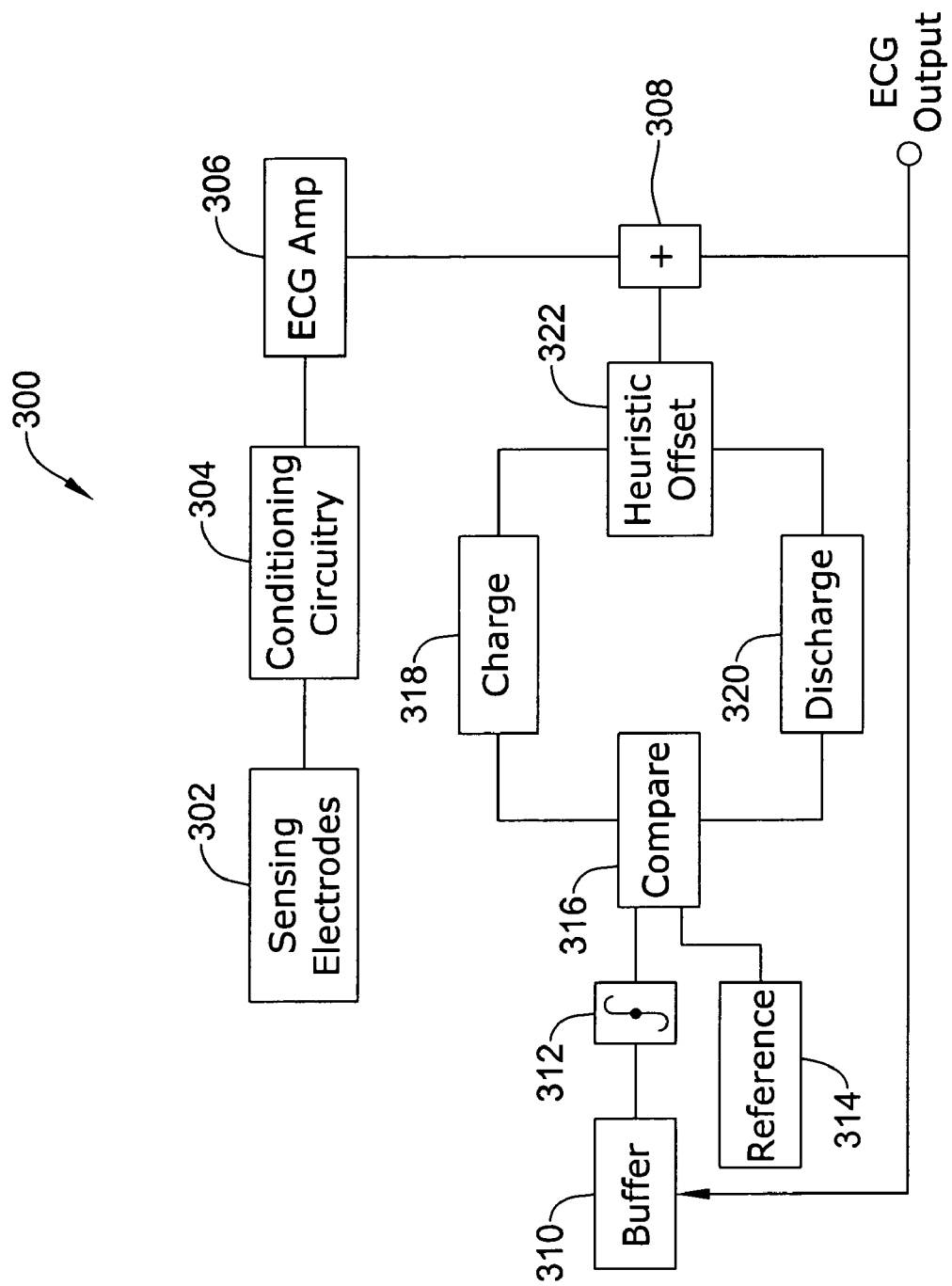
FIG. 19 illustrates an analog circuit for providing a heuristic filter.

FIG. 19 illustrates an analog circuit for providing a heuristic filter. The circuit 300 receives signal sensing electrodes 302 with conditioning circuitry 304 which in turn provides a signal to the ECG amplifier 306. The ECG amplifier 306 feeds a summer 308, which ultimately provides the ECG output. A feedback signal is taken by a buffer 310 that feeds a decaying integrator 312 (in the simplest case, the integrator 312 may be a simple RC circuit). The output of integrator 312 is compared to a stored value 314 using a comparator 316. The comparator 316 either charges 318 or discharges 320 a heuristic offset 322 depending on whether the integrator 312 provides an output that is greater than or less than the stored value 314. The heuristic offset 322 is then fed into the summer 308.

The circuit operates by observing the average value of the ECG output, as indicated by the integrator 312. Depending on the characteristics of the integrator 312 and/or buffer 310, the stored value 314 is selected to correspond to a desired quiescent point for the ECG output. The comparator 316 either increases or decreases the heuristic offset 322 in response to this comparison, thus adjusting the average ECG output. Additional circuitry may be included to increase accuracy and/or stability. If desired, rather than charging or discharging, the comparator 316 may feed an accumulator that provides a digital input to a digital-to-analog converter (DAC) that provides the heuristic offset 322 to the summer 308. In short, a feedback signal is used to center the average ECG output.

Figure 20:
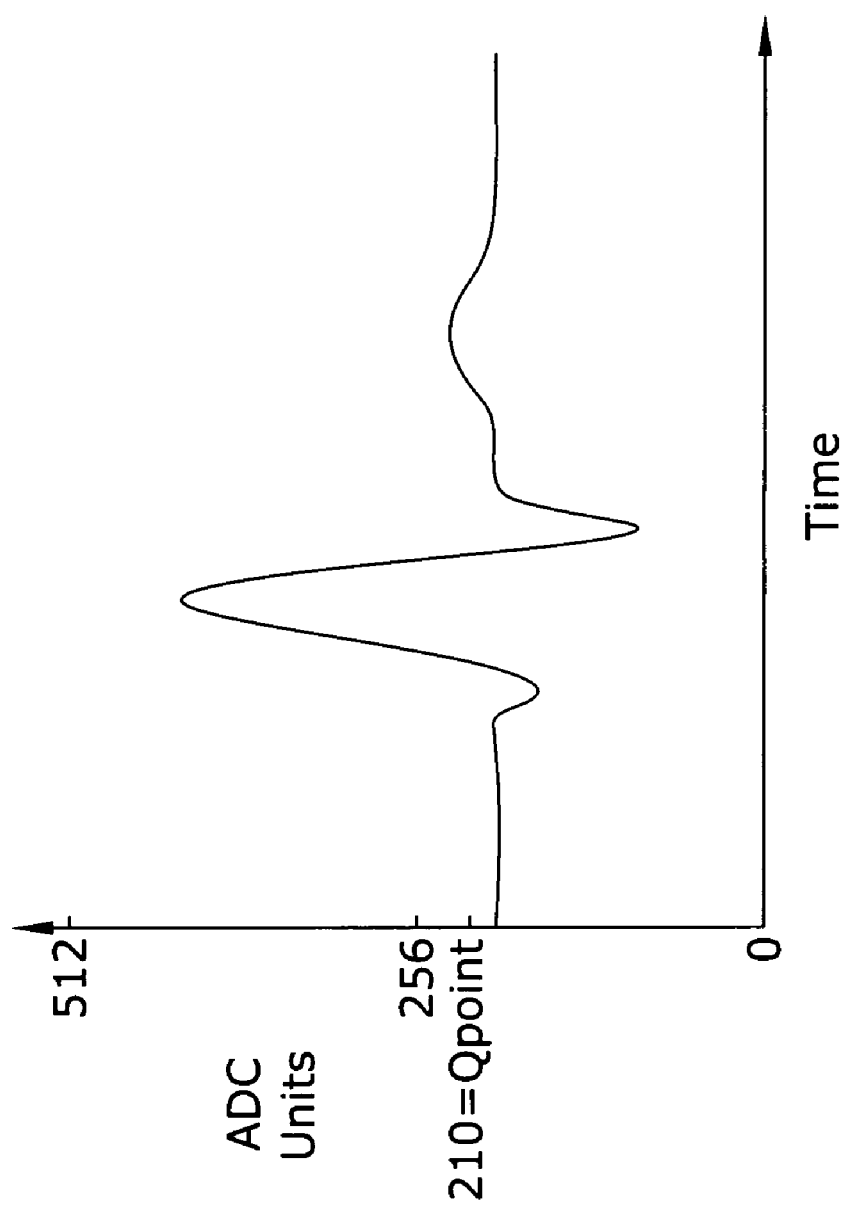
FIG. 20 illustrates a method wherein the quiescent point is not centered on the ADC scale.

FIG. 20 illustrates the selection of a quiescent point that is off-center relative to the dynamic range of an ADC. For example, some patients demonstrate a cardiac signal that has a greater excursion in one direction than the other. This is shown in FIG. 20 where a positive excursion is substantially higher in amplitude than the negative excursion of the signal. To maximize the use of the dynamic range, this signal is placed such that the Q-point is below the center point of the ADC dynamic range. In the illustrative example, the quiescent point is selected at 210 ADC units for a 9-bit scale having a maximum range from 0-512 units.

The methods set forth above may be implemented by the use of any appropriate hardware including logic devices, controllers, processors and other suitable analog and/or digital devices or circuits. The present invention may be embodied in a software product stored on readable media including magnetic, electric and optically readable media.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of cardiac signal analysis comprising:
   capturing a cardiac signal using implanted electrodes;
   conditioning and amplifying the signal;
   performing analog-to-digital conversion on the signal; and
   applying a heuristic filter to the captured cardiac signal by repeatedly performing the following at a predetermined interval:
   a) calculating an actual quiescent point of the analog-to-digital converted signal; and
   b) adjusting the analog-to-digital conversion of the signal to modify the actual quiescent point toward a desired quiescent point; and
   adjusting the predetermined interval by calculating a quiescent distance between the actual quiescent point and the desired quiescent point; and:
   x) reducing the predetermined interval if the quiescent distance is greater than a first threshold;
   y) increasing the predetermined interval if the quiescent distance is less than a second threshold; or
   z) if the quiescent distance is between the first and second thresholds, making no adjustment to the predetermined interval.

2. The method of claim 1, wherein:
   the step of performing analog-to-digital conversion includes converting the captured cardiac signal to a series of digital values stored on an accumulator; and
   the step of adjusting the analog-to-digital conversion is performed by modifying a value stored on the accumulator at periodic intervals.

3. The method of claim 2, wherein the step of calculating an actual quiescent point is performed by averaging several values stored on the accumulator.

4. The method of claim 1, wherein:
   the step of adjusting the analog-to-digital conversion is performed by generating a heuristic offset and adding the heuristic offset to the digitally converted cardiac signal to generate an adjusted digital representation of the captured cardiac signal; and
   the actual quiescent point is calculated by observing a value of at least one sample of the adjusted digital representation.

5. The method of claim 1 wherein the analog-to-digital conversion of the signal includes sampling the signal using a sampling interval, and further wherein the sampling interval is not the same as the predefined interval.

6. The method of claim 5 wherein the step of adjusting the predefined interval selects from a range of interval values that includes values that are greater than the sampling interval and values that are less than the sampling interval.

7. A method of cardiac signal analysis comprising:
   capturing a cardiac signal between implanted electrodes;
   conditioning the cardiac signal for use in analysis, including sampling the cardiac signal;
   creating an adjusted signal, the adjusted signal representing a series of samples of the conditioned cardiac signal added to an offset;
   repeatedly performing at predefined intervals:
   a) calculating an average of the adjusted signal over a predetermined period of time; and
   b) modifying the offset depending upon whether the average of the adjusted signal is greater than or less than a predetermined value; and
   using the calculated average of the adjusted signal to adjust the predefined intervals by:
   increasing the duration of the predefined intervals if the calculated average is close to a desired quiescent point; or
   decreasing the duration of the predefined intervals if the calculated average is greater than a desired quiescent point.

8. A method of treating a patient using an implanted cardiac stimulus device system, the method comprising:
   utilizing a first method of cardiac signal analysis during a first time period;
   delivering cardiac stimulus; and
   during a second time period following delivery of the cardiac stimulus, performing the method of claim 7.

9. The method of claim 8, further comprising:
   during the second time period, comparing the adjusted signal to a predetermined threshold to detect a threshold crossing;
   ending the second time period when a threshold crossing is detected.

10. An implantable cardiac rhythm management device comprising:
    at least a pair of sensing electrodes;
    an analog-to-digital converter (ADC) configured to convert a signal received from the sensing electrodes into a digital representation; and
    control circuitry coupled to the ADC that is configured to:
    a) perform the following steps repeatedly at a predefined interval:
    calculate an actual quiescent point of the ADC output;
    calculate a quiescent distance from the actual quiescent point to a desired quiescent point; and
    increment or decrement a counter in the ADC to reduce the quiescent distance; and
    b) at a fixed interval, compare the quiescent distance to a first threshold and a second threshold and
    if the quiescent distance is shorter than the first threshold, increase the duration of the predetermined interval;
    if the quiescent distance is longer than the second threshold, decrease the duration of the predetermined interval; else
    leave the predetermined interval unchanged.

11. The device of claim 10 wherein the analog-to-digital converter is configured to use a sampling interval that is not the same as the predefined interval.

12. The device of claim 11 wherein the control circuitry is configured such that the step of adjusting the predefined interval selects from a range of interval values that includes values that are greater than the sampling interval and values that are less than the sampling interval.

* * * * *

UNITED STATES PATENT AND TRADEMARK OFFICE
CERTIFICATE OF CORRECTION

| | | |
|---|---|---|
| PATENT NO. | : 7,623,913 B2 | Page 1 of 1 |
| APPLICATION NO. | : 11/497204 | |
| DATED | : November 24, 2009 | |
| INVENTOR(S) | : Phillips | |

It is certified that error appears in the above-identified patent and that said Letters Patent is hereby corrected as shown below:

On Title page,

[*] Notice: Subject to any disclaimer, the term of this patent is extended or adjusted under 35 USC 154(b) by 501 days Delete the phrase "by 501 days" and insert -- by 616 days --

Signed and Sealed this

Eleventh Day of May, 2010

David J. Kappos
*Director of the United States Patent and Trademark Office*